United States Patent [19]

Jinbo et al.

[11] Patent Number: 5,907,039
[45] Date of Patent: May 25, 1999

[54] AMINO ALCOHOL DERIVATIVE AND METHOD FOR PREPARING THE SAME

[75] Inventors: Masayuki Jinbo, Tokyo; Hidekazu Oyamada, Saitama; Jinichi Inokuchi, Tokyo, all of Japan

[73] Assignee: Seikagaku Kogyo Kabushiki Kaisha, Tokyo, Japan

[21] Appl. No.: 08/761,934

[22] Filed: Dec. 9, 1996

[30] Foreign Application Priority Data

Dec. 8, 1995 [JP] Japan ..................................... 7-345080

[51] Int. Cl.$^6$ ...................... C07D 207/12; C07D 207/14; C07D 211/12; C07D 223/04
[52] U.S. Cl. .......................... 540/609; 546/246; 546/247; 548/566; 548/567; 548/569; 548/950; 548/967
[58] Field of Search ............................ 540/609; 546/246, 546/247; 548/566, 567, 569, 950, 967

[56] References Cited

U.S. PATENT DOCUMENTS 5,041,441  8/1991  Radin et al. .......................... 514/237.8

FOREIGN PATENT DOCUMENTS

| 0765865 | 4/1997 | European Pat. Off. . |
|---|---|---|
| 4025330 | 2/1992 | Germany . |
| 9505177 | 2/1995 | WIPO . |
| 9534530 | 12/1995 | WIPO . |
| WO9534530 | 12/1995 | WIPO . |

OTHER PUBLICATIONS

Jin–ichi Inokuchi et al., "Preparation of the Active Isomer of 1–phenyl–2–decanoylamino–3–morpholino–1–propanol, inhibitor of murine glucocerebroside synthetase" *J. of Lipid Research*, 28:565–571 (1987).

Akira Abe et al., "Structural and stereochemical studies of potent inhibitors of glucosylceramide synthase and tumor cell growth" *J. of Lipid Research*, 36:611–621 (1995).

Norman S. Radin et al., "Metabolic Effects of Inhibiting Glycoslyceramide Synthesis with PDMP and Other Substance" *Advances of Lipid Research* 26:183–213 (1993).

Quanying Liu et al. "Lewis Acid Induced Rearrangement of 2,3–Epoxy Amines; Characterisation of Aziridinium Ion Intermediates and Regiospecific Ring Opening with Nitrogen Nucleophiles", *J. Chem. Soc. Perkin Trans.* 1:1363–1365 (1994).

Williams et al. "Syntheses of some substituted 1–phenyl–2, 3–diamino–1–propanols from α–halogen substituted Mannich bases", *J. of the Am. Chem. Soc.*, 74(15):3875–3877 (1952).

Bruce A. Fenderson et al. "A Ceramide Analogue (PMDP) Inhibits Glycolipid synthesis in Fish Embryos" *Experimental Cell Research*, 198(2):362–366 (1992).

R.R. Vunnam et al. "A New Class of Monoamine Oxidase Inhibitors", *J. of Neurochemistry*, 34(2):410–416, (1980).

Robin Polt et al. "Aluminoxy Acetals from α–Amino esters: Chirality Transfer via Sequential Addition of Hydride and C–Nucleophiles. 2–Amino Alcohols and Sphingosines", *J. Org. Chem.*, 57(20):5469–5480, (1992).

Manfred E. Wolff et al. "Synthesis of Some 1–Phenyl–2–amino–3–substituted–amino–1–propanols from α–Oximino Mannich Bases", *J. of the Am. Chem Soc.*, 78:(11)2615:2618, (1956).

Akira Abe et al. "Improved Inhibitors of Glucosylceramide Synthase" *J. Biochem.* 111:191–196 (1992).

Gerald Brenner–Weib et al. "Synthesis of Potential Inhibitors of the Glycosphingolipid Biosynthesis" *Tetrahedron Letter* 48(28):5855–5860 (1992).

Kenneth G. Carson et al. "Studies on Morpholinosphingolipids Potent Inhibitors of Glycosylceramide Synthase" *Tetrahedron Letters* 35(17):2659–2662 (1994).

Norman S. Radin et al. "Metabolic Effects of Inhibiting Glycosylceramide Synthesis with PDMP and Other Substance" *Advances of Lipid Research* 26:183–213 (1993).

CA 51:3495, Chemical Abstracts, Mar. 1957.

CA 51:1190, Chemical Abstracts, Jan. 1957.

CA 107:7603, Chemical Abstracts, Abstract for JP 61145148, 1987.

Loudon, Solid–Phase Peptide Synthesis, Organic Chemistry, pp. 1347–1352, 1984.

Morrison et al., Organic Chemistry, Fourth Edition, pp. 206 and 902–903, 1987.

Fieser et al., Reagents for Organic Synthesis, pp. 109–110, 1967.

*Primary Examiner*—Mukund J. Shah
*Assistant Examiner*—Deepak R. Rao
*Attorney, Agent, or Firm*—Sughrue, Mion, Zinn, Macpeak & Seas, PLLC

[57] ABSTRACT

Amino alcohol derivatives with a primary amino group or a substituted amino group influence the synthesis of glycolipids and have antiviral, antitumor, metastasis inhibiting and neural cell growth enhancing functions. The amino alcohol derivatives are useful in preparing 2-acylamino alcohol derivatives.

6 Claims, No Drawings

AMINO ALCOHOL DERIVATIVE AND METHOD FOR PREPARING THE SAME

FIELD OF THE INVENTION

The present invention relates to a method for preparing 2-acylamino alcohol derivatives which have a function to enhance or inhibit biosynthesis of glycolipids and also have antiviral, antitumor, metastasis inhibition and nerve cell growth enhancing functions. Furthermore, the present invention relates to novel amino alcohol derivatives which are useful in preparing the 2-acylamino alcohol derivatives.

BACKGROUND OF THE INVENTION

A 2-acylamino alcohol derivative, 2-decanoylamino-3-morpholino-1-phenyl-1-propanol (hereinafter referred to as "PDMP"), represented by the following formula:

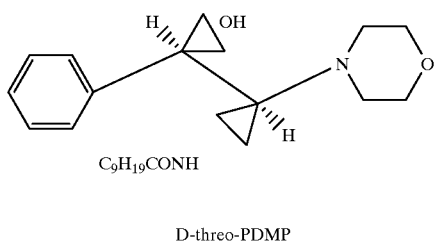

D-threo-PDMP has an activity to control biosynthesis of glycolipids, but the activity is greatly different among its four stereoisomers. Therefore, separation of its optically active isomers is carried out by a method in which decanoylaminoacetophenone is condensed with morpholine by Mannich reaction and then reduced with sodium borohydride to obtain PDMP as a mixture of four stereoisomers, resolution of the diastereomers is effected by a crystallization method and then optical resolution of the racemic compounds is effected by a crystallization method (*J. Lipid. Res.*, 28:565–571 (1987), and *Advances in Lipid Research*, 26:183–213 (1993)).

SUMMARY OF THE INVENTION

An object of the present invention is to provide a process for preparing optic ally active substances of PDMP having plural asymmetric centers and its analogues using a chiral compound as the starting material at high efficiency, particularly a stereoselective synthesis process which requires no complicated optical resolution step.

Another object of the present invention is to provide novel amino alcohol derivatives which are useful for preparing PDMP and its analogues.

In order to develop a simple and general stereoselective process for preparing PDMP and its analogues, the inventors of the present invention have conducted intensive studies and found as the results that all of the four stereoisomers of PDMP or its analogues can be stereoselectively synthesized by establishing synthetic steps which comprise stereochemically proceeding reactions using, as the main starting material and asymmetric source, an N-protected-2-aminopropanediol which has two asymmetric centers in its molecule in advance and whose amino group is protected with a urethane type protecting group which can be obtained at a reasonable price as a reagent for peptide synthesis use, and have also found novel amino alcohol derivatives as intermediates of the synthetic steps. The present invention has been accomplished based on these findings.

Accordingly, these and other objects of the present invention have been accomplished by a process for preparing a 2-acylamino alcohol derivative which comprises the following steps:

(A) reacting an aminopropanol derivative represented by the following formula (1):

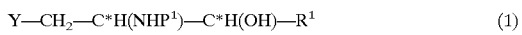

wherein * represents an asymmetric carbon atom;
$P^1$ represents an alkyl group or an amino-protecting group;
$R^1$ represents an alkyl group, a cycloalkyl group or an aryl group; and
Y represents a leaving group, with an amine represented by $R^2H$, wherein $R^2$ is represented by the following formula (I) to (VI), to synthesize an amino alcohol derivative represented by the following formula (2):

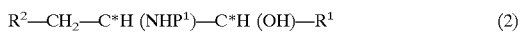

wherein $P^1$, $R^1$ and $R^2$ each has the same meaning as those defined above, (B) leaving $P^1$ from said amino alcohol derivative represented by formula (2) to synthesize an amino alcohol derivative represented by the following formula (3):

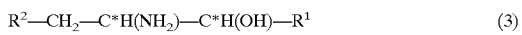

wherein $R^1$ and $R^2$ each has the same meaning as those defined above, and (C) reacting said amino alcohol derivative represented by formula (3) with a carboxylic acid represented by $R^{11}COOH$ or a reactive derivative thereof, wherein $R^{11}$ represents an alkyl or alkenyl group having from 3 to 18 carbon atoms which may be substituted with a hydroxyl group, to prepare a 2-acylamino alcohol derivative represented by the following formula (4):

wherein $R^1$, $R^2$ and $R^{11}$ each has the same meaning as those defined above;

(I)

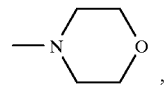

(II)

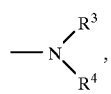

(III)

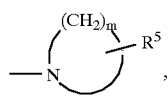

-continued

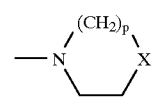
(IV)

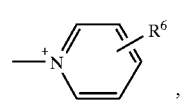
(V)

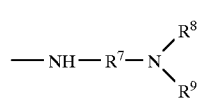
(VI)

wherein R³ and R⁴ are the same or different and each represents a hydrogen atom, a lower alkyl group, a lower alkenyl group, a hydroxyl-lower-alkyl group, a lower alkoxyalkyl group, an amino-lower-alkyl group, a cycloalkyl group, a hydroxycycloalkyl group, an aralkyl group or a piperazino group which may be substituted with a lower alkyl group;

R⁵ represents a hydrogen atom or at least one substituents which are the same or different and are selected from a hydroxyl group, a lower alkyl group , a lower alkoxyl group, a hydroxyl-lower-alkyl group, a carboxyl group, a (lower alkoxyl)carbonyl group, an aralkyl group, a piperidino group, an acyloxy group, an amino group and an amino-lower-alkyl group;

R⁶ represents a hydrogen atom or at least one substituents which are the same or different and are selected from the substituents as defined in R⁵;

R⁷ represents a lower alkylene group which may be discontinued by an oxygen atom;

R⁸ and R⁹ are the same or different and each represents a hydrogen atom, a lower alkyl group or a hydroxyl-lower-alkyl group, or R⁸ and R⁹ represent, together with a nitrogen atom to which they are bound, a piperidino group or a morpholino group which may be substituted with a lower alkyl group;

m is an integer of 2 to 6;

p is an integer of 2 or 3; and x represents the following formula (VII) or (VIII):

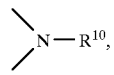
(VII)

(VIII)

wherein R¹⁰ represents a hydrogen atom, a lower alkyl group, an acyl group, a (lower alkoxyl) carbonyl group or a pyridyl group.

Furthermore, these and other objects of the present invention have been accomplished by the amino alcohol derivatives represented by formula (2).

Moreover, these and other objects of the present invention have been accomplished by the amino alcohol derivatives represented by formula (3).

DETAILED DESCRIPTION OF THE INVENTION

In the present invention, the term "lower" in the "lower alkyl", "lower alkoxyl" and the like means that the carbon number thereof is from 1 to 6.

Also, the term "alkylene group which may be discontinued by an oxygen atom" means that at least two alkylene groups are linked to each other via at least one oxygen atom.

PDMP and its analogues, have been discovered as glycolipid biosynthesis controlling substances are interesting compounds which also have physiological functions such as antiviral, antitumor, metastasis inhibition, nerve cell growth enhancing and the like. Structurally, they have 2-amino alcohol as the basic nucleus and at least two asymmetric carbon atoms in the molecule. Since functions of four stereoisomers obtained therefrom are different from each other, it is necessary to develop a means for the stereoselective synthesis of these four isomers in studying relationship between structure and function of PDMP and its analogues and developing high active analogues.

As described above, one aspect of the present invention relates to a process for stereoselectively synthesizing the four stereoisomers of PDMP and its analogues using, as the main starting material, a 2-aminopropanediol derivative which has two asymmetric carbon atoms in its molecule and whose amino group is protected with a urethane type protecting group. This process is based on the following new findings.

That is, the stereoselective synthesis of PDMP and its analogues has been achieved by 1) using a chiral compound having two asymmetric carbon atoms in its molecule as the starting material, 2) introducing a leaving group (a mesyl group or the like) into only primary hydroxyl group among primary and secondary hydroxyl groups, and then substituting the leaving group with a primary or secondary amine and 3) constructing all of the reaction steps as keeping the stereochemistry.

The present invention will be described according to the following synthetic steps.

Synthetic Steps:

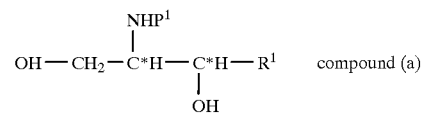   compound (a)

step 1  YCl  (ex. CH₃SO₂Cl)

-continued

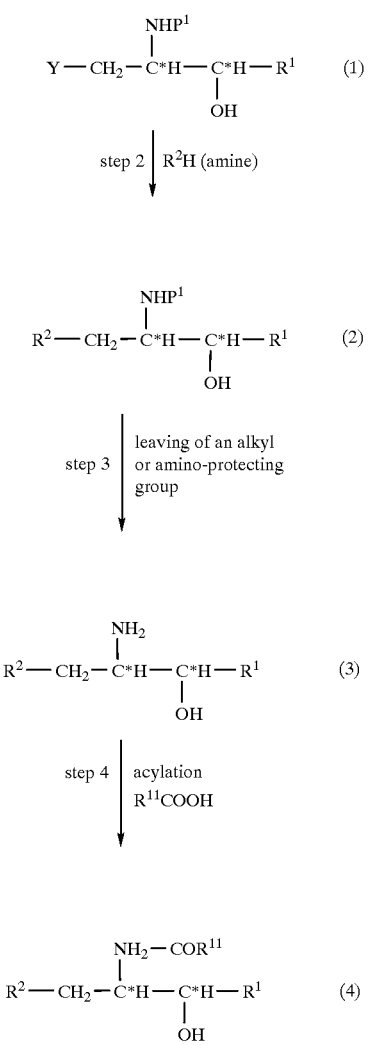

step 2 | R²H (amine)

step 3 | leaving of an alkyl or amino-protecting group step 4 | acylation R¹¹COOH According to the process of the present invention, an optically active aminopropanol derivative represented by formula (1) is used as the starting material. In formula (1), $R^1$ is an alkyl group, a cycloalkyl group or an aryl group having from 6 to 15 carbon atoms such as phenyl or the like, preferably a phenyl group which may be substituted with 1 to 3 substituents which are the same or different and are selected from a lower alkyl group, a lower alkoxyl group, a hydroxyl group, a hydroxyl-lower-alkyl group and a nitro group (e.g., a phenyl group, a dimethoxyphenyl group, a dihydroxyphenyl group), and more preferably a phenyl group. $P^1$ is an alkyl group having from 3 to 18 carbon atoms such as a decyl group or an amino-protecting group (e.g., a benzyloxycarbonyl group which may be substituted with a nitro group, a halogen atom, a lower alkoxyl group, a (lower alkoxyl)phenylazo group or a phenylazo group; an alkoxycarbonyl group containing a straight, branched or cyclic alkyl group having from 1 to 15 carbon atoms which may be substituted with a fluorenyl group or a methylsulfonyl group; or the like). Specific examples thereof include benzyloxycarbonyl groups which may have a substituent(s) (e.g., a benzyloxycarbonyl group, a p-nitrobenzyloxycarbonyl group, a p-bromobenzyloxycarbonyl group, a p-methoxybenzyloxycarbonyl group, a p-methoxyphenylazobenzyloxycarbonyl group and the like), alkoxycarbonyl groups which may have a substituent(s) (e.g., a t-butoxycarbonyl group, a cyclopentyloxycarbonyl group, an octyloxycarbonyl group, a 9-fluorenylmethoxycarbonyl group, a methylsulfonylethoxycarbonyl group and the like) and amino-protecting groups such as a benzenesulfonyl group and the like. Y represents a leaving group such as a methanesulfonyl (mesyl) group, a trihalogenomethanesulfonyl group (e.g., a trifluoromethanesulfonyl group), a p-toluenesulfonyl group, a benzenesulfonyl group, a p-bromobenzenesulfonyl group or the like.

The aminopropanol derivatives represented by formula (1) can be obtained by treating the optically active N-protected-2-aminopropanediol shown in the above synthesis steps as "compound (a)" with methanesulfonyl chloride (Ms—Cl) or the like in a solvent (e.g., pyridine or the like) or in an anhydrous solvent (e.g., dichloromethane or the like) in the presence of pyridine at a range between an ice-cooled temperature and room temperature to effect methanesulfonylation (mesylation) of only primary hydroxyl group of the diol (step 1). The compound represented by formula (2) can be prepared by treating the product obtained in step 1 after isolation, or without isolation in some cases, with an amine represented by formula $R^2H$ in an organic solvent (e.g., ethyl alcohol, N,N-dimethylformamide or the like) (step 2). In the amine represented by formula $R^2H$, $R^2$ represents a group represented by formula (I) to (VI) described above and in formula (I) to (VI), carbon numbers of a cycloalkyl group or a hydroxycycloalkyl group are from 3 to 8 and those of an aralkyl group are from 6 to 20. Preferably, $R^2$ is a morpholino group, a (lower alkyl)amino group, a (morpholino-lower alkyl)amino group, a cycloalkylamino group which may be substituted with a hydroxyl group, a pyrrolidino group which may be substituted with a hydroxyl group or a hydroxyl-lower-alkyl group, a piperazino group which may be substituted with a lower alkyl group, a bis(hydroxyl-lower-alkyl)amino group or a piperidino group which may be substituted with a hydroxyl group or a hydroxyl-lower-alkyl group, and more preferably a morpholino group or a pyrrolidino group.

In step 3, the alkyl group or amino-protecting group which protects the amino group is removed by a usual method such as catalytic reduction, acid treatment, base treatment or the like to obtain the compound represented by formula (3). Next, the amino group thus formed is acylated with a carboxylic acid represented by formula $R^{11}COOH$ or a reactive derivative thereof such as an acid halide or acid anhydride of a carboxylic acid or the like to obtain the 2-acylamino alcohol derivative represented by formula (4) (step 4). In the above formula $R^{11}COOH$, $R^{11}$ is an alkyl or alkenyl group having from 3 to 18 carbon atoms which may have a hydroxyl group at the 2- or 3-position. When the acyl group ($R^{11}CO$—) to be introduced has 10 carbon atoms, decanoyl chloride or decanoic anhydride is used as the above-described acylating agent. Alternatively, the objective 2-acylamino alcohol derivative represented by formula (4) can be obtained by reacting the compound represented by formula (3) with a carboxylic acid ($R^{11}COOH$) having from 8 to 16 carbon atoms and a condensing agent usually used in an amido bonding reaction (step 4). Examples of the carboxylic acid include fatty acids and hydroxyl-substituted fatty acids such as octanoic acid, 2-hydroxyoctanoic acid, decanoic acid, 2-hydroxydecanoic acid, dodecanoic acid, 2-hydroxydodecanoic acid, myristic acid, 2-hydroxymyristic acid, palmitic acid, 2-hydroxypalmitic acid and the like. Examples of the condensing agent include dicyclohexylcarbodiimide, water-soluble carbodiimide and the like. Examples of the water-soluble carbodiimide include 1-ethyl-3-(3-dimethylaminopropyl)carbodiimide hydrochloride (EDC).

Examples of the amino alcohol derivatives represented by formula (2) include
(a) derivative wherein $R^1$ is an alkyl group or a cycloalkyl group, or a phenyl group which may be substituted with from 1 to 3 substituents which are the same or different and are selected from a lower alkyl group, a lower alkoxyl group, a hydroxyl group, a hydroxyl-lower-alkyl group and a nitro group; and $P^1$ is an alkyl group having from 3 to 18 carbon atoms or an amino-protecting group selected from (i) a benzyloxycarbonyl group which may be substituted with a nitro group, a halogen atom, a lower alkoxyl group, a (lower alkoxyl)phenylazo group or a phenylazo group and (ii) an alkoxycarbonyl group containing a straight, branched or cyclic alkyl group which may be substituted with a fluorenyl group or a methylsulfonyl group,
(b) derivatives wherein $R^1$ is an alkyl group having from 6 to 15 carbon atoms, a cyclohexyl group or a phenyl group; $P^1$ is a decyl group or an amino-protecting group selected from a benzyloxycarbonyl group, a t-butoxycarbonyl group and an octyloxycarbonyl group; and $R^2$ is an amino group selected from a morpholino group, a (lower alkyl)amino group, a (morpholino-lower alkyl)amino group, a cycloalkylamino group which may be substituted with a hydroxyl group, a pyrrolidino group which may be substituted with a hydroxyl group or a hydroxyl-lower-alkyl group, a piperazino group which may be substituted with a lower alkyl group, a bis(hydroxyl-lower-alkyl)amino group and a piperidino group which may be substituted with a hydroxyl group or a hydroxyl-lower-alkyl group,
(c) derivatives wherein $R^1$ is a phenyl group; $P^1$ is a benzyloxycarbonyl group; and $R^2$ is a morpholino group, a pyrrolidino group, a hydroxypyrrolidino group, a hydroxypiperidino group, an N-methylpiperazino group, a diethanolamino group or a hydroxycyclohexylamino group; and wherein their configuration is (1S,2S), and
(d) derivatives wherein $R^1$ is a phenyl group; $P^1$ is a benzyloxycarbonyl group; and $R^2$ is a morpholino group, a pyrrolidino group, a piperidino group, a cyclohexylamino group or a cyclopentylamino group; and wherein their configuration is (1R,2R).

Examples of the amino alcohol derivatives represented by formula (3) include derivatives wherein $R^1$ is an alkyl group having from 6 to 15 carbon atoms, a cyclohexyl group or a phenyl group; and $R^2$ is a morpholino group, a (lower alkyl)amino group, a (morpholino-lower alkyl)amino group, a cycloalkylamino group which may be substituted with a hydroxyl group, a pyrrolidino group which may be substituted with a hydroxyl group or a hydroxyl-lower-alkyl group, a piperazino group which may be substituted with a lower alkyl group, a bis(hydroxyl-lower-alkyl)amino group or a piperidino group which may be substituted with a hydroxyl group or a hydroxyl-lower-alkyl group.

According to the present invention, the product of each production step may be isolated. In some cases, the objective 2-acylamino alcohol derivative represented by formula (4) can be obtained by using as the starting material an optically active diol which is the raw material of formula (1), and carrying out the above-described stepwise reactions in succession without isolating the product of each step.

The synthesis methods of N-protected-2-aminopropanediols to be used as the raw material of the amino alcohol derivative represented by formula (1) which is the starting material in the process of the present invention include a method in which an aminoketone is reduced (*J. Org. Chem.*, 54:1866 (1989)), a method in which an N-(diphenylmethylene)amino acid ester is treated with diisobutylaluminum hydride and then with a Grignard's reagent (*J. Org. Chem.*, 57:5469 (1992)), a method in which an acid chloride of an N-protected-aminoaldehyde or N-protected-amino acid is treated with an organometallic reagent (*J. Am. Chem. Soc.*, 95:4098 (1973)), an asymmetric aldol reaction of 2-oxazolidinone with aldehyde (*J. Am. Chem. Soc.*, 108:6757 (1986)) (Evans method) and an asymmetric aldol reaction of chiral imidazolidinone and oxazolidinone with aldehyde (*Helv. Chem. Acta*, 70:237 (1987)).

On the other hand, N-protected-α-aminoketones to be used as the raw material of N-protected-2-aminopropanediols may be synthesized, for example, by a method in which an N-protected-α-amino acid is used as the starting material, and the carboxyl group of the amino acid is converted into an acid chloride and then allowed to undergo Friedel-Crafts' reaction with benzene (*J. Am. Chem. Soc.*, 103:6157 (1981)) or a method in which the carboxyl group of the amino acid is treated with an alkyl lithium reagent to convert it into a lithium salt and then allowed to react with a Grignard's reagent (*J. Org. Chem.*, 54:1866 (1989)).

Thus, according to the present invention, optically active substances of PDMP and its analogues having a plurality of asymmetric centers can be synthesized efficiently by using an N-protected-2-aminopropanol derivative as the starting material without requiring complex optical resolution. In other words, the present invention is markedly useful, because all of the four stereoisomers of PDMP and its analogues can be synthesized stereoselectively. In addition, the novel amino alcohol derivatives of the present invention have plural asymmetric centers and therefore are markedly useful as a synthesis intermediate of PDMP and its analogues.

The present invention is now illustrated in greater detail by way of the following examples, but it should be understood that the present invention is not to be construed as being limited thereto. The term "MeOH", "AcOEt", "AcOH" and "DMF" as used hereinafter mean "methanol", "ethyl acetate", "acetic acid" and "N,N-dimethylformamide", respectively.

EXAMPLES

Example 1

Synthesis of (1S, 2S)-2-benzyloxycarbonylamino-1-phenyl-1,3-propanediol-3-methanesulfonyl ester:

(1S,2S)-2-Benzyloxycarbonylamino-1-phenyl-1,3-propanediol (21.2 g, 70.3 mmol) was dissolved in pyridine (350 ml), and methanesulfonyl chloride (5.6 ml, 72.3 mmol) was added dropwise thereto on an ice bath over a period of 5 minutes. The resulting mixture was stirred for 30 minutes on the ice bath and then overnight at room temperature. After confirming completion of the reaction with TLC (chloroform:methanol=20:1), the solvent was removed by evaporation, and ethyl acetate (500 ml) was added thereto. The residue thus obtained was washed with 1N HCl (250 ml×3 times) and brine (250 ml), and then dried over anhydrous sodium sulfate to evaporate the solvent. The crystals thus precipitated were washed with a mixture of ethyl acetate and n-hexane (1:1) to obtain the objective compound as white crystals (25.3 g, yield: 95.0%).

TLC Rf: 0.55 (CHCl$_3$:MeOH=20:1), 0.83 (AcOEt), 0.62 (n-Hexane:AcOEt=1:2); $^1$H-NMR (CDCl$_3$) δ:
7.35–7.26 (10H, m, aromatic), 5.30 (1H, d, J=7.81 Hz, NH), 5.02 (2H, s, C$\underline{H_2}$—O—CO), 4.99 (1H, d, J=3.91 Hz, C$\underline{H}$—OH), 4.43–4.39, 4.22–4.12 (3H, m, N—C$\underline{H}$—C$\underline{H}_2$), 2.98 (3H, S, SO$_3$CH$_3$)

Example 2
Synthesis of (1S, 2S)-2-benzyloxycarbonylamino-1-phenyl-1,3-propanediol-3-methanesulfonyl ester:

(1S,2S)-2-Benzyloxycarbonylamino-1-phenyl-1,3-propanediol (15.4 g, 51.0 mmol) was dissolved in methylene chloride (150 ml), pyridine (12.1 ml, 149.6 mmol) was added thereto, and then methanesulfonyl chloride (4.5 ml, 58.1 mmol) was added dropwise thereto on an ice bath over a period of 5 minutes. The mixture thus prepared was stirred for 30 minutes on the ice bath and then overnight at room temperature. After confirming completion of the reaction with TLC (chloroform:methanol=20:1, n-hexane:ethyl acetate=1:1), water (100 ml) and chloroform (50 ml) were added thereto. The resulting organic layer was washed with each 100 ml of 1N hydrochloric acid, water, a saturated sodium bicarbonate solution and water in this order, dried over anhydrous sodium sulfate and then filtered. The solvent was removed by evaporation, and 100 ml of a mixture of n-hexane and ethyl acetate (2:1) was added thereto and allowed to stand overnight. The crystals thus precipitated were collected by filtration and washed with a mixture of n-hexane and ethyl acetate (2:1) to obtain the objective compound as white crystals (16.56 g, yield: 85.7%).

Example 3
Synthesis of (1S, 2S)-2-benzyloxycarbonylamino-3-morpholino-1-phenyl-1-propanol:

(1S,2S)-2-Benzyloxycarbonylamino-1-phenyl-1,3-propanediol-3-methanesulfonyl ester (9.68 g, 25.5 mmol) was dissolved in ethanol (50 ml), morpholine (9.8 ml, 112.6 mmol) was added thereto at room temperature, and the obtained mixture was stirred at 40° C. for 3 days. After confirming completion of the reaction with TLC (chloroform:methanol=20:1, n-hexane:ethyl acetate=1:2, ethyl acetate), the solvent was removed by evaporation, and then water (50 ml) and ethyl acetate (150 ml) were added thereto. The resulting organic layer was washed with a saturated sodium bicarbonate solution, water and brine in this order, dried over anhydrous sodium sulfate and then filtered. The solvent was removed by evaporation and the resulting residue was purified by silica gel column chromatography (n-hexane:ethyl acetate=1:2) to obtain the objective compound as a colorless oily material (3.61 g, yield: 38.1%).

TLC Rf: 0.32 (CHCl$_3$:MeOH=20:1), 0.12 (n-Hexane:AcOEt=1:2) $^1$H-NMR (CDCl$_3$) δ: 7.38–7.26 (10H, m, aromatic), 5.04 (2H, s, CH$_2$O—CO), 5.00 (1H, d, J=3.41 Hz, H-1), 4.11 (1H, m, H-2), 3.72 (4H, m, (CH$_2$)$_2$O), 2.68–2.47 (6H, m, (CH$_2$)$_3$N)

Example 4
Synthesis of (1R,2R)-2-benzyloxycarbonylamino-3-morpholino-1-phenyl-1-propanol:

(1R,2R)-2-Benzyloxycarbonylamino-1-phenyl-1,3-propanediol-3-methanesulfonyl ester (1.21 g, 3.19 mmol) was dissolved in N,N-dimethylformamide (6 ml), morpholine (1.11 g, 12.8 mmol) was added thereto at room temperature, and the mixture thus obtained was stirred at 40° C. for 24 hours. After confirming almost completion of the reaction with TLC (chloroform:methanol=20:1, n-hexane:ethyl acetate=1:2, ethyl acetate), a saturated sodium bicarbonate solution (70 ml) and ethyl acetate (100 ml) were added thereto, and the resulting organic layer was washed with water and brine in this order, dried over anhydrous sodium sulfate and then filtered. The solvent was removed by evaporation and the resulting residue was purified by silica gel column chromatography (n-hexane:ethyl acetate=1:2) to obtain the objective compound as a colorless oily material (507.5 mg, yield: 43.0%).

Example 5
Synthesis of (1S,2S)-2-amino-3-morpholino-1-phenyl-1-propanol:

(1S,2S)-2-Benzyloxycarbonylamino-3-morpholino-1-phenyl-1-propanol (438.8 mg, 1.19 mmol) was dissolved in methanol (10 ml), 10% palladium-carbon (126.5 mg, 10.0 mol %) was added thereto, and the mixture thus obtained was stirred overnight at room temperature in an atmosphere of hydrogen. After confirming completion of the reaction with TLC (chloroform: methanol=9:1 and 7:3), palladium-carbon was removed by filtration and the resulting filtrate was concentrated to obtain the objective compound as a colorless oily material (275.6 mg, yield: 98.5%).

TLC Rf: 0.48, 0.24 (CHCl$_3$:MeOH=7:3) (tailing), 0.68 (CHCl$_3$:MeOH:aqNH$_3$=4:1: trace); $^1$H-NMR (CD$_3$OD) δ: 7.36–7.26 (5H, m, aromatic), 4.47 (1H, d, J=6.60 Hz, H-1), 3.65 (4H, m, (CH$_2$)$_2$O), 3.21–3.14 (1H, m, H-2), 2.51–2.43, 2.32–2.24, 2.11–2.05 (6H, m, (CH$_2$)$_3$N)

Example 6
Synthesis of (1S,2S)-2-amino-3-morpholino-1-phenyl-1-propanol:

(1S,2S)-2-Benzyloxycarbonylamino-3-morpholino-1-phenyl-1-propanol (3.82 g, 10.3 mmol) was dissolved in methanol (10 ml), ammonium formate (2.6 g, 41.3 mmol) and 10% palladium-carbon (888.5 mg, 8.09 mol %) were added thereto, and the mixture thus obtained was stirred overnight at room temperature. After confirming completion of the reaction with TLC (chloroform:methanol=9:1 and 7:3), palladium-carbon was removed by filtration and the resulting filtrate was concentrated to obtain the objective compound as a colorless oily material (2.34 g, yield: 99.0%).

Example 7
Synthesis of (1S,2S)-2-decanoylamino-3-morpholino-1-phenyl-1-propanol:

(1S,2S)-2-Amino-3-morpholino-1-phenyl-1-propanol (1.33 g, 4.0 mmol) was dissolved in methanol (4 ml), and decanolyl chloride (0.82 ml, 4.0 mmol) was added thereto in the presence of triethylamine (668.0 μl, 4.8 mmol) under ice cooling. Thirty minutes thereafter, almost completion of the reaction was confirmed with TLC (ethyl acetate, chloroform:methanol=20:1, chloroform:methanol=7:3), and then methanol (30 ml) was added thereto and allowed to stand for 90 minutes. After concentration of the reaction solution under a reduced pressure, a saturated sodium bicarbonate solution (20 ml) was added thereto, and extraction was conducted with ethyl acetate (50 ml). The resulting organic layer was washed with water (20 ml) and brine (20 ml), dried over anhydrous sodium sulfate and then concentrated under a reduced pressure to obtain an oily material (853.5 mg). The oily material thus obtained was purified by silica gel column chromatography (ethyl acetate) to obtain the objective compound as a colorless oily material (930.5 mg, yield: 59.6%).

TLC Rf: 0.62 (CHCl$_3$:MeOH=9:1), 0.26 (AcOEt); $^1$H-NMR (CDCl$_3$) δ: 7.38–7.26 (5H, m, aromatic), 5.87 (1H, d, J=7.26 Hz, NH), 4.95 (1H, d, J=3.63 Hz, H-1), 4.28 (1H, m, H-2), 3.72 (4H, m, (CH$_2$)$_2$O), 2.63–2.44 (6H, m, (CH$_2$)$_3$N), 2.09 (2H, m, CO—C$\underline{H}_2$—CH$_2$), 1.50 (2H, m, CO—CH$_2$—C$\underline{H}_2$), 1.24 (12H, brs, (C$\underline{H}_2$)$_6$CH$_3$), 0.88 (3H, t, CH$_3$)

Example 8
Synthesis of (1S,2S)-2-decanoylamino-3-morpholino-1-phenyl-1-propanol:

(1S,2S)-2-Amino-3-morpholino-1-phenyl-1-propanol (84.9 mg, 0.270 mmol) was dissolved in tetrahydrofuran (4 ml), decanoic anhydride (109.2 mg, 0.334 mmol) was added thereto in the presence of triethylamine (80.0 μl, 0.575 mmol) under ice cooling, and the mixture thus obtained was stirred for one day at room temperature. After confirming almost completion of the reaction with TLC (ethyl acetate, chloroform:methanol=20:1, chloroform:methanol=7:3), ethyl acetate (30 ml) and a saturated sodium bicarbonate solution (20 ml) were added thereto, and the resulting organic layer was washed with water (20 ml) and brine (20 ml), dried over anhydrous sodium sulfate and then concentrated under a reduced pressure to obtain an oily material (130.8 mg). The thus obtained oily material was purified by silica gel column chromatography (ethyl acetate) to obtain the objective compound as a colorless oily material (37.2 mg, yield: 40.5%).

Example 9
Synthesis of (1S, 2S)-2-decanoylamino-3-morpholino-1-phenyl-1-propanol:

(1S,2S)-2-Benzyloxycarbonylamino-1-phenyl-1,3-propanediol-3-methanesulfonyl ester (9.5 g, 25.1 mmol) was dissolved in ethanol (50 ml) on an oil bath (40° C.), morpholine (8.7 ml, 100 mmol) was added thereto, and the mixture thus obtained was stirred at 40° C. for 3 days. After confirming almost completion of the reaction with TLC (n-hexane:ethyl acetate=1:2), the solvent was removed by evaporation under a reduced pressure. Ethyl acetate (100 ml) was added to the resulting residue, and the crystals thus precipitated were removed by filtration. The resulting filtrate was washed with a saturated sodium bicarbonate solution (50 ml), water (50 ml×2 times) and brine (50 ml) and then dried over anhydrous sodium sulfate. The solvent was removed by evaporation under a reduced pressure to obtain an oily material (13.7 g).

Methanol (50 ml) and 10% palladium-carbon (2.3 g, 8.6 mol %) were added to the oily material, and vigorously stirred overnight in an atmosphere of hydrogen. After confirming completion of the reaction with TLC (ethyl acetate, chloroform:methanol=9:1, chloroform:methanol=7:3), palladium-carbon was removed by filtration and the resulting filtrate was concentrated to obtain an oily material (9.33 g).

The oily material thus obtained was dissolved in methanol (25 ml), triethylamine (4.2 ml, 30 mmol) was added thereto, and then decanoyl chloride (5.15 ml, 25 mmol) was added dropwise thereto under ice cooling. Thirty minutes thereafter, it was confirmed that the reaction was almost completed with TLC (ethyl acetate, chloroform:methanol=20:1, chloroform:methanol=7:3), and then methanol (20 ml) was added thereto and allowed to stand for 30 minutes. The reaction solution was concentrated under a reduced pressure, a saturated sodium bicarbonate solution (50 ml) was added thereto, and extraction was conducted with ethyl acetate (150 ml). The resulting organic layer was washed with water (40 ml×3 times) and brine (40 ml), dried over anhydrous sodium sulfate and then concentrated under a reduced pressure to obtain an oily material (9.73 g). Thereafter, the oily material was purified by silica gel column chromatography (ethyl acetate) to obtain the objective compound as a colorless oily material (4.35 g, yield: 44.6%).

Example 10
Synthesis of (1S,2S,2'S)-2-(2'-hydroxydecanoylamino)-3-morpholino-1-phenyl-1-propanol and (1S,2S,2'R)-2-(2'-hydroxydecanoylamino)-3-morpholino-1-phenyl-1-propanol:

(1S,2S)-2-Amino-3-morpholino-1-phenyl-1-propanol (141.5 mg, 0.600 mmol) was dissolved in methylene chloride (6 ml), 2-hydroxydecanoic acid (100 mg, 0.531 mmol) and N-hydroxysuccinimide (150.8 mg, 1.131 mmol) were added thereto, and the mixture thus obtained was stirred at room temperature for 15 minutes. 1-Ethyl-3-(3-dimethylaminopropyl)carbodiimide hydrochloride (134.0 mg, 0.699 mmol) was added thereto on an ice bath and stirred overnight. After confirming almost completion of the reaction with TLC (ethyl acetate, chloroform:methanol=20:1), ethyl acetate (30 ml) was added thereto, the resulting organic layer was washed with a 5% citric acid solution (15 ml), a saturated sodium bicarbonate solution (15 ml) and water (15 ml) in this order and dried over anhydrous sodium sulfate, the solvent was removed by evaporation under a reduced pressure. The crude product thus obtained was purified by silica gel column chromatography (ethyl acetate, chloroform:methanol=20:1) to obtain the objective compounds as colorless oily materials (15.6 mg as the (1S,2S,2'S) compound and 20.0 mg as the (1S,2S,2'R) compound). In this case, absolute configuration of the objective compounds were identified by carrying out the same synthetic procedure using (2R)-2-hydroxydecanoic acid as the raw material.

(1S,2S,2'S)-2-(2'-Hydroxydecanoylamino)-3-morpholino-1-phenyl-1-propanol:

TLC Rf: 0.38 (AcOEt); $^1$H-NMR (CDCl$_3$) δ: 7.36–7.25 (5H, m, aromatic), 6.82 (1H, d, J=7.81 Hz, NH), 4.96 (1H, d, J=3.41 Hz, H-1), 4.3 (1H, m, H-2), 3.99 (1H, dd, J=3.90, 3.91 Hz, H-2'), 3.71 (4H, t, (CH$_2$)$_2$O), 2.64–2.49 (6H, m, (CH$_2$)$_3$N), 1.70–1.65 (1H, m, CH(OH)—CH$_2$(A)), 1.50–1.43 (1H, m, CH(OH)—CH$_2$(B)), 1.31–1.20 ($\overline{12H}$, m, (CH$_2$)$_6$—CH$_3$), 0.88 (3H, t, $\overline{CH_3}$); $^{13}$C-NMR(CDCl$_3$) δ: 17$\overline{4.3}$, 140.8, 128.4, 127.7, 126.0, 75.2, 72.0, 66.9, 59.9, 54.4, 51.0, 34.8, 31.8, 29.4, 29.2, 24.8, 22.6, 14.1

(1S,2S,2'R)-2-(2'-Hydroxydecanoylamino)-3-morpholino-1-phenyl-1-propanol:

TLC Rf: 0.20 (AcOEt); $^1$H-NMR (CDCl$_3$) δ: 7.37–7.25 (5H, m, aromatic), 6.88 (1H, d, J=8.3 Hz, NH), 5.00 (1H, d, J=3.41 Hz, H-1), 4.3 (1H, m, H-2), 4.03 (1H, dd, J=3.90, 3.42 Hz, H-2'), 3.72 (4H, t, (CH$_2$)$_2$O), 2.67–2.53 (6H, m, (CH$_2$)$_3$N), 1.66–1.61 (1H, m, CH(OH)—CH$_2$(A)), 1.50–1.45 (1H, m, CH(OH)—CH$_2$(B)), 1.32–1.20 ($\overline{12H}$, m, (CH$_2$)$_6$CH$_3$), 0.88 (3H, t, CH$_3$); $^{13}$C-NMR(CDCl$_3$) δ: 174.0, 14$\overline{0.8}$, 128.4, 127.7, 126.0, 75.2, 72.2, 66.9, 60.1, 54.4, 50.8, 34.8, 31.8, 29.4, 29.3, 29.2, 24.6, 22.6, 14.1

Example 11
Synthesis of (1S, 2S)-2-decanoylamino-3-(N-methylpiperazino)-1-phenyl-1-propanol:

(1S,2S)-2-Benzyloxycarbonylamino-1-phenyl-1,3-propanediol-3-methanesulfonyl ester (1.81 g, 4.78 mmol) was dissolved in ethanol, N-methylpiperazine (1.92 g, 19.2 mmol) was added thereto, and the mixture thus obtained was stirred at 40° C. for 3 days. After completion of the reaction, the solvent was removed by evaporation under a reduced pressure, a saturated sodium bicarbonate solution was added thereto, and extraction was conducted with chloroform. The resulting organic layer was dried over anhydrous sodium sulfate and filtered, and then the solvent was removed by evaporation. Next, the extract was dissolved in methanol, 10% palladium-carbon was added thereto and a hydrogen gas was introduced under stirring vigorously. After completion of the reaction, palladium-carbon was removed by filtration, the solvent was removed by evaporation under a reduced pressure, methanol was added to the resulting residue, and decanoyl chloride was further added thereto on an ice bath in the presence of triethylamine. After completion of the reaction, the solvent was removed by evaporation under a reduced pressure, a saturated sodium bicarbonate solution was added thereto, and extraction was conducted with chloroform. The organic layer thus obtained was dried over anhydrous sodium sulfate and filtered, and the solvent was removed by evaporation. The extract was purified by silica gel column chromatography (chloroform:methanol= 9:1) to obtain the objective compound as a colorless oily material (10.0 mg).

$^1$H-NMR (CDCl$_3$) δ: 7.37–7.25 (5H, m, aromatic), 5.91 (1H, d, J=7.3 Hz, NH), 4.95 (1H, d, J=3.4 Hz, H-1), 4.29 (1H, m, H-2), 2.78–2.36 (10H, m, H-3, H-2', H-3', H-4', H-5'), 2.32 (3H, t, N—CH$_3$), 2.30–2.27 (1H, m, COCH$_2$(A)), 2.11–2.08 (1H, m, COCH$_2$(B)), 1.63–1.60 (1H, m, CO—CH$_2$—CH$_2$(A)), 1.53–1.48 (1H, m, CO—CH$_2$—CH$_2$(B)), 1.25 (12H, brs, (CH$_2$)$_6$CH$_3$), 0.88 (3H, t, CH$_3$)

Example 12
Synthesis of (1S,2S)-2-decanoylamino-3-((2S)-2-hydroxymethylpyrrolidino)-1-phenyl-1-propanol:

The objective compound (89.6 mg) was prepared as a colorless oily material in the same manner as in Example 11, except that (2S)-2-hydroxymethylpyrrolidine was used in place of N-methylpiperazine.

$^1$H-NMR (CDCl$_3$) δ: 7.35–7.23 (5H, m, aromatic), 6.13 (1H, d, J=6.3 Hz, NH), 4.99 (1H, d, J=3.4 Hz, H-1), 4.14 (1H, m, H-2), 3.71–3.67 (1H, m, H-6'A), 3.57–3.53 (1H, m, H-6'B), 3.29–3.24 (1H, m, H-5'A), 3.14–3.09 (1H, m, H-3A), 2.83–2.78 (1H, m, H-3B), 2.76 (1H, m, H-2'), 2.38–2.32 (1H, m, H-5'B), 2.14–2.03 (2H, m, COCH$_2$), 1.92–1.83 (1H, m, H-3'A), 1.80–1.73 (2H, m, H-4'), 1.70–162 (1H, m, H-3'B), 1.50–1.43 (2H, m, CO—CH$_2$—CH$_2$), 1.22 (12H, brs, (CH$_2$)$_6$CH$_3$), 0.88 (3H, t, CH$_3$); $^{13}$C-NMR(CDCl$_3$) δ: 174.1, 141.1, 128.3, 127.5, 125.7, 75.6, 66.4, 63.6, 57.6, 56.1, 54.1, 36.7, 31.8, 29.4, 29.3, 29.2, 29.0, 27.0, 25.6, 23.9, 22.6, 14.1

Example 13
Synthesis of (1S,2S)-2-decanoylamino-3-(3-hydroxypyrrolidino)-1-phenyl-1-propanol:

The objective compound (a mixture having a diastereomer ratio of 1:1, 88.3 mg) was prepared as a colorless oily material in the same manner as in Example 11, except that 3-hydroxypyrrolidine was used in place of N-methylpiperazine. $^1$H-NMR (CDCl$_3$) δ: 7.36–7.24 (5H, m, aromatic), 5.91 (0.5H, d, J=7.3 Hz, NH), 5.88 (0.5H, d, J=7.3 Hz, NH), 5.0 (1H, H-1), 4.40 (1H, m, H-3'), 4.23 (1H, m, H-2), 3.06–3.01 (1H, m, H-5'A), 3.00–2.70 (3H, m, H-3, H-2'A), 2.67–2.63 (1H, m, H-2'B), 2.54–2.45 (1H, m, H-5'B), 2.21–2.12 (1H, m, H-4'A), 2.11–2.00 (2H, m, COCH$_2$), 1.79–1.74 (1H, m, H-4'B), 1.50–1.44 (2H, m, CO—CH$_2$-CH$_2$), 1.22 (12H, brs, (CH$_2$)$_6$CH$_3$), 0.88 (3H, t, CH$_3$); $^{13}$C-NMR(CDCl$_3$) δ: 173.6, 141.0, 140.9, 128.3, 127.5, 127.4, 125.9, 75.3, 75.1, 71.1, 71.0, 63.7, 57.6, 53.6, 53.5, 52.6, 36.7, 34.7, 31.8, 29.4, 29.3, 29.2, 29.0, 25.6, 22.6, 14.0

Example 14
Synthesis of (1S,2S)-2-decanoylamino-3-pyrrolidino-1-phenyl-1-propanol:

The objective compound (92.2 mg) was prepared as a colorless oily material in the same manner as in Example 11, except that pyrrolidine was used in place of N-methylpiperazine.

$^1$H-NMR (CDCl$_3$) δ: 7.36–7.23 (5H, m, aromatic), 5.91 (1H, d, J=7.8 Hz, NH), 5.05 (1H, d, J=3.4 Hz, H-1), 4.26 (1H, m, H-2), 2.86 (2H, d, J=5.4 Hz, H-3), 2.70 (4H, m, H-2', H-5'), 2.07 (2H, m, COCH$_2$), 1.81 (4H, m, H-3', H-4'), 1.47 (2H, m, CO—CH$_2$—CH$_2$), 1.3–1.1 (12H, m, (CH$_2$)$_6$CH$_3$), 0.88 (3H, t, CH$_3$); $^{13}$C-NMR(CDCl$_3$) δ: 173.5, 141.0, 128.2, 127.4, 125.9, 75.4, 57.9, 55.2, 52.3, 36.7, 31.8, 29.3, 29.2, 29.0, 25.6, 23.6, 22.6, 14.0

Example 15
Synthesis of (1S,2S)-2-decanoylamino-3-(3-hydroxymethylpiperidino)-1-phenyl-1-propanol:

The objective compound (a mixture having a diastereomer ratio of 1:1, 246.5 mg) was prepared as a colorless oily material in the same manner as in Example 11, except that 3-hydroxymethylpiperidine was used in place of N-methylpiperazine.

$^1$H-NMR (CDCl$_3$) δ: 7.36–7.24 (5H, m, aromatic), 5.96 (0.5H, d, J=7.8 Hz, NH), 5.94 (0.5H, d, J=7.8 Hz, NH), 4.96 (0.5H, d, J=3.4 Hz, H-1), 4.94 (0.5H, d, J=3.4 Hz, H-1), 4.33–4.26 (1H, m, H-2), 3.59–3.51 (1H, m), 3.50–3.42 (1H, m), 3.00–2.83 (2H, m), 2.59 (1H, dd, H-3A), 2.48 (1H, dd, H-3B), 2.3–2.0 (2H, m), 2.07 (2H, m, COCH$_2$), 1.9–1.5 (4H, m), 1.48 (2H, m, CO—CH$_2$—CH$_2$), 1.4–1.1 (12H, m, (CH$_2$)$_6$CH$_3$), 1.10–1.00 (1H, m), 0.88 (3H, t, CH$_3$)

Example 16
Synthesis of (1S,2S)-3-cyclohexylamino-2-decanoylamino-1-phenyl-1-propanol:

The objective compound (40.6 mg) was prepared as a colorless oily material in the same manner as in Example 11, except that cyclohexylamine was used in place of N-methylpiperazine.

$^1$H-NMR (CDCl$_3$) δ: 7.4–7.2 (5H, m, aromatic), 6.64 (1H, d, J=7.3 Hz, NH), 5.14 (1H, d, J=2.5 Hz, H-1), 4.37 (1H, m, H-2), 3.34 (1H, dd, J=4.9, 12.7 Hz, H-3A), 3.13 (1H, dd, J=5.4, 16.3 Hz, H-3B), 2.77 (1H, m, (CH$_2$)$_2$CHNH), 2.2–2.0 (4H, m), 1.76 (2H, d, J=12.7 Hz), 1.63 (1H, d, J=10.7 Hz), 1.5–1.0 (19H, m), 0.88 (3H, t, J=6.8 Hz, CH$_3$); $^{13}$C-NMR (CDCl$_3$) δ: 173.7, 141.1, 128.3, 127.3, 125.5, 75.9, 57.0, 53.2, 49.1, 36.8, 33.2, 33.0, 31.8, 29.4, 29.3, 29.2, 29.0, 25.8, 25.7, 24.8, 22.6, 14.1

Example 17
Synthesis of (1S,2S)-2-decanoylamino-3-(4-hydroxycyclohexylamino)-1-phenyl-1-propanol:

The objective compound (12.0 mg) was prepared as a colorless oily material in the same manner as in Example 11, except that 4-hydroxycyclohexylamine was used in place of N-methylpiperazine.

$^1$H-NMR (CDCl$_3$) δ: 7.4–7.2 (5H, m, aromatic), 6.36 (1H, d, J=6.8 Hz, NH), 5.13 (1H, d, J=2.0 Hz, H-1), 4.31 (1H, m, H-2), 3.61 (1H, m, CH$_2$CHOH)), 3.34 (1H, dd, J=4.4, 12.7 Hz, H-3A), 3.06 (1H, dd, J=4.9, 12.7 Hz, H-3B), 2.73 (1H, m, CH$_2$CHNH), 2.2–1.9 (6H, m), 1.5–1.0 (18H, m), 0.88 (3H, t, J=6.8 Hz, CH$_3$)

Example 18
Synthesis of (1S,2S)-2-decanoylamino-3-(2-(N-morpholino)ethylamino-1-phenyl-1-propanol:

The objective compound (91.7 mg) was prepared as a colorless oily material in the same manner as in Example 11, except that 2-(N-morpholino)ethylamine was used in place of N-methylpiperazine.

$^1$H-NMR (CDCl$_3$) δ: 7.4–7.2 (5H, m, aromatic), 6.02 (1H, d, J=7.3 Hz, NH), 4.64 (1H, d, J=2.4 Hz, H-1), 4.28 (1H, m, H-2), 3.80 (1H, dd, J=9.8, 14.2 Hz), 3.68 (4H, t, J=4.4 Hz, CH$_2$—O—CH$_2$), 3.50 (2H, m), 3.30 (1H, dd, J=5.9, 14.2 Hz), 2.7–2.5 (2H, m), 2.48 (4H, t, J=4.4 Hz, CH$_2$NCH$_2$), 2.4–2.3 (2H, m), 2.00 (2H, m, COCH$_2$), 1.65 (2H, m), 1.5–1.0 (14H, m, (CH$_2$)$_7$CH$_3$), 0.88 (3H, t, J=6.8 Hz, CH$_3$)

Example 19
Synthesis of (1S,2S)-2-(2-hydroxy-n-octanoylamino)-3-morpholino-1-phenyl-1-propanol:

(1S,2S)-2-Amino-3-morpholino-1-phenyl-1-propanol was prepared in the same manner as in Example 11, except that morpholine was used in place of N-methylpiperazine. The compound obtained (99.2 mg, 0.42 mmol) was dissolved in methylene chloride, 2-hydroxy-n-octanoic acid (80.0 mg, 0.50 mmol) and N-hydroxysuccinimide (102.1 mg, 0.42 mmol) were added thereto at room temperature, and then 1-ethyl-3-(3-dimethylaminopropyl)carbodiimide hydrochloride (118.1 mg, 0.62 mmol) was added thereto under ice cooling and further stirred. After completion of the reaction, chloroform was added thereto and the resulting organic layer was washed with a 5% citric acid solution, a saturated sodium bicarbonate solution and water in this order, dried over anhydrous sodium sulfate and then filtered. The solvent was removed by evaporation, and the resulting residue was purified by silica gel column chromatography (ethyl acetate) to obtain the objective compound as a colorless oily material as one of its diastereomer (15.4 mg), as well as the other diastereomer (16.9 mg).
(One diastereomer)

TLC Rf: 0.2 (AcOEt); $^1$H-NMR (CDCl$_3$) δ: 7.37–7.26 (5H, m, aromatic), 6.75 (1H, d, J=7.3 Hz, NH), 5.00 (1H, d, J=3.4 Hz, H-1), 4.3 (1H, m, H-2), 4.02, 4.01, 4.00, 3.99 (1H, dd, CO—CH—OH), 3.74, 3.73, 3.72 (4H, t, CH$_2$OCH$_2$), 2.69–2.52 (6H, m, CH$_2$N(CH$_2$)$_2$), 1.72–1.66 (1H, m, CH(OH)CH$_2$(A)), 1.51–1.43 (1H, m, CH(OH)CH$_2$(B)), 1.30–1.20 (8H, m, (CH$_2$)$_4$CH$_3$), 0.87 (3H, t, CH$_3$); $^{13}$C-NMR(CDCl$_3$) δ: 174.1, 140.8, 128.4, 127.7, 126.0, 75.3, 72.0, 66.9, 60.0, 54.5, 51.1, 34.9, 31.6, 29.0, 24.7, 22.5, 14.0
(The other diastereomer)

TLC Rf: 0.1 (AcOEt); $^1$H-NMR (CDCl$_3$) δ: 7.37–7.26 (5H, m, aromatic), 6.85 (1H, d, J=7.8 Hz, NH), 5.01 (1H, d, J=3.4 Hz, H-1), 4.3 (1H, m, H-2), 4.06, 4.05, 4.04, 4.03 (1H, dd, CO—CH—OH), 3.74, 3.73, 3.72 (4H, t, CH$_2$OCH$_2$), 2.68–2.51 (6H, m, CH$_2$N(CH$_2$)$_2$), 1.68–1.64 (1H, m, CH(OH)CH$_2$(A)), 1.51–1.46 (1H, m, CH(OH)CH$_2$(B)), 1.30–1.20 (8H, m, (CH$_2$)$_4$CH$_3$), 0.88 (3H, t, CH$_3$); $^{13}$C-NMR(CDCl$_3$) δ: 173.9, 140.8, 128.4, 127.7, 126.0, 75.2, 72.2, 66.9, 60.1, 54.4, 50.8, 34.8, 31.6, 29.0, 24.5, 22.5, 14.0

Example 20
Synthesis of (1R,2S)-2-decanoylamino-3-(4-hydroxypiperidino)-1-phenyl-1-propanol:

The objective compound (204.2 mg) was prepared as white solid in the same manner as in Example 11, except that (1R,2S)-2-benzyloxycarbonylamino-1-phenyl-1,3-propanediol-3-methanesulfonyl ester was used in place of (1S,2S)-2-benzyloxycarbonylamino-1-phenyl-1,3-propanediol-3-methanesulfonyl ester, and 4-hydroxypiperidine was used in place of N-methylpiperazine.

TLC Rf: 0.24 (CHCl$_3$:MeOH:AcOH=9:1:1); $^1$H-NMR (CDCl$_3$) δ: 7.37–7.26 (5H, m, aromatic), 6.29 (1H, d, J=4.3 Hz, NH), 4.83 (1H, d, J=5.0 Hz, H-1), 4.25 (1H, m, H-2), 3.76 (1H, m, H-4'), 2.90–2.78 (2H, br, H-2'A), 2.70–2.56 (2H, m, H-3), 2.38–2.35 (2H, br, H-2'B), 2.01–1.91 (2H, br, H-3'A), 2.16–2.10 (2H, m, COCH$_2$), 1.67–157 (4H, m, H-3'B, COCH$_2$CH$_2$), 1.24 (12H, brs, (CH$_2$)$_6$CH$_3$), 0.88 (3H, t, CH$_3$); MS (FAB): 405 (M+H)$^+$

Example 21
Synthesis of (1S,2R)-2-decanoylamino-3-(4-hydroxypiperidino)-1-phenyl-1-propanol:

The objective compound (160.5 mg) was prepared as a colorless oily material in the same manner as in Example 20, except that (1S,2R)-2-benzyloxycarbonylamino-1-phenyl-1,3-propanediol-3-methanesulfonyl ester was used in place of (1R,2S)-2-benzyloxycarbonylamino-1-phenyl-1,3-propanediol-3-methanesulfonyl ester.

$^1$H-NMR (CDCl$_3$) δ:
Coincided with the data of Example 20.

Example 22
Synthesis of (1R,2R)-2-decanoylamino-3-(4-hydroxypiperidino)-1-phenyl-1-propanol:

The objective compound (184.2 mg) was prepared as a colorless oily material in the same manner as in Example 20, except that (1R,2R)-2-benzyloxycarbonylamino-1-phenyl-1, 3-propanediol-3-methanesulfonyl ester was used in place of (1R,2S)-2-benzyloxycarbonylamino-1-phenyl-1,3-propanediol-3-methanesulfonyl ester.

TLC Rf: 0.20 (CHCl$_3$:MeOH:AcOH=9:1:1); $^1$H-NMR (CDCl$_3$) δ: 7.37–7.23 (5H, m, aromatic), 6.77 (1H, d, J=7.6 Hz, NH), 4.95 (1H, d, J=3.6 Hz, H-1), 4.41 (1H, m, H-2), 3.78 (1H, m, H-4'), 3.06–3.03 (2H, br, H-2'A), 2.86 (2H, m, H-3), 2.80–2.70 (2H, br, H-2'B), 2.10–2.00 (4H, m, H-3'A, COCH$_2$), 1.76 (2H, m, H-3'B), 1.45 (2H, m, COCH$_2$CH$_2$), 1.24 (12H, brs, (CH$_2$)$_6$CH$_3$), 0.88 (3H, t, CH$_3$); $^{13}$C-NMR (CDCl$_3$) δ: 174.8, 141.0, 128.8, 128.1, 126.4, 74.5, 65.1, 58.2, 51.2, 50.9, 50.7, 36.9, 32.6, 32.3, 29.9, 29.8, 29.7, 29.6, 26.0, 23.0, 14.6; MS (FAB): 405 (M+H)$^+$

Example 23
Synthesis of (1R,2S)-2-decanoylamino-3-diethylamino-1-phenyl-1-propanol:

The objective compound (L-erythro compound) was prepared in the same manner as in Example 11, except that (1R,2S)-2-benzyloxycarbonylamino-1-phenyl-1,3-propanediol-3-methanesulfonyl ester was used in place of (1S,2S)-2-benzyloxycarbonylamino-1-phenyl-1,3-propanediol-3-methanesulfonyl ester, and diethylamine was used in place of N-methylpiperazine.

TLC Rf: 0.59 (CHCl$_3$:MeOH:AcOH=9:1:1), 0.32 (CHCl$_3$: MeOH:AcOH=95:5:10); $^1$H-NMR (CDCl$_3$) δ: 7.38–7.23 (5H, m, aromatic), 5.87 (1H, d, J=4.0 Hz, NH), 4.75 (1H, d, J=6.3 Hz, H-1), 4.17 (1H, m, H-2), 2.97–2.50 (6H, m, CH$_2$N(CH$_2$)$_2$), 2.04 (2H, m, COCH$_2$), 1.45 (2H, COCH$_2$CH$_2$), 1.24 (12H, brs, (CH$_2$)$_6$CH$_3$), 1.05 (6H, brt, N(CH$_2$CH$_2$)$_2$), 0.88 (3H, t, (CH$_2$)$_6$CH$_3$); MS (FAB): 377 (M+H)$^+$

Example 24
Synthesis of (1S,2R)-2-decanoylamino-3-diethylamino-1-phenyl-1-propanol:

The objective compound (D-erythro compound) was prepared in the same manner as in Example 11, except that (1S,2R)-2-benzyloxycarbonylamino-1-phenyl-1,3-propanediol-3-methanesulfonyl ester was used in place of (1S,2S)-2-benzyloxycarbonylamino-1-phenyl-1,3-propanediol-3-methanesulfonyl ester, and diethylamine was used in place of N-methylpiperazine.

$^1$H-NMR (CDCl$_3$) δ:
Coincided with the data of Example 23.

Example 25
Synthesis of (1R,2S)-2-hexanoylamino-3-(4-hydroxypiperidino)-1-phenyl-1-propanol:

The objective compound (250.5 mg) was prepared as white solid in the same manner as in Example 20, except that hexanoyl chloride was used in place of decanoyl chloride.

$^1$H-NMR (CDCl$_3$) δ: 7.36–7.26 (5H, m, aromatic), 5.95 (1H, d, J=4.3 Hz, NH), 4.80 (1H, d, J=5.0 Hz, H-1), 4.22 (1H, m, H-2), 3.72 (1H, m, H-4'), 2.90–2.78 (2H, br, H-2'A), 2.70–2.56 (2H, m, H-3), 2.38–2.35 (2H, br, H-2'B), 2.01–1.91 (2H, br, H-3'A), 2.16–2.10 (2H, m, COCH$_2$), 1.67–1.57 (4H, m, H-3'B, COCH$_2$CH$_2$), 1.24 (4H, brs, (CH$_2$)$_2$CH$_3$), 0.88 (3H, t, CH$_3$)

Example 26
Synthesis of (1R,2S)-2-octanoylamino-3-(4-hydroxypiperidino)-1-phenyl-1-propanol:

The objective compound (230.2 mg) was prepared as white solid in the same manner as in Example 20, except that octanoyl chloride was used in place of decanoyl chloride.

$^1$H-NMR (CDCl$_3$) δ: 7.36–7.26 (5H, m, aromatic), 6.09 (1H, d, J=4.3 Hz, NH), 4.80 (1H, d, J=5.0 Hz, H-1), 4.21 (1H, m, H-2), 3.70 (1H, m, H-4'), 2.90–2.78 (2H, br, H-2'A), 2.70–2.56 (2H, m, H-3), 2.38–2.35 (2H, br, H-2'B), 2.01–1.91 (2H, br, H-3'A), 2.16–2.10 (2H, m, COCH$_2$), 1.67–1.57 (4H, m, H-3'B, COCH$_2$CH$_2$), 1.24 (8H, brs, (CH$_2$)$_4$CH$_3$), 0.88 (3H, t, CH$_3$)

Example 27
Synthesis of (1R,2S)-2-dodecanoylamino-3-(4-hydroxypiperidino)-1-phenyl-1-propanol:

The objective compound (265.0 mg) was prepared as white solid in the same manner as in Example 20, except that dodecanoyl chloride was used in place of decanoyl chloride.

$^1$H-NMR (CDCl$_3$) δ: 7.36–7.26 (5H, m, aromatic), 5.97 (1H, d, J=4.3 Hz, NH), 4.80 (1H, d, J=5.0 Hz, H-1), 4.22 (1H, m, H-2), 3.72 (1H, m, H-4'), 2.90–2.78 (2H, br, H-2'A), 2.70–2.56 (2H, m, H-3), 2.38–2.35 (2H, br, H-2'B), 2.01–1.91 (2H, br, H-3'A), 2.16–2.10 (2H, m, COCH$_2$), 1.67–1.57 (4H, m, H-3'B, COCH$_2$CH$_2$), 1.24 (16H, brs, (CH$_2$)$_8$CH$_3$), 0.88 (3H, t, CH$_3$)

Examples 28 to 30

The following stereoisomers were prepared in the same manner as in Examples 25 to 27. The yield amounts were as follows.

Example 28;
(1S,2R)-2-hexanoylamino-3-(4-hydroxypiperidino)-1-phenyl-1-propanol; yield amount: 245.0 mg Example 29:
(1S,2R)-2-octanoylamino-3-(4-hydroxypiperidino)-1-phenyl-1-propanol; yield amount: 233.5 mg Example 30:
(1S, 2R)-2-dodecanoylamino-3-(4-hydroxypiperidino)-1-phenyl-1-propanol; yield amount: 215.0 mg

Example 31
Synthesis of (1R, 2R)-2-benzyloxycarbonylamino-3-pyrrolidino-1-phenyl-1-propanol (1R,2R)-2-Benzyloxycarbonylamino-1-phenyl-1,3-propanediol-3-methanesulfonyl ester (1.52 g, 4.01 mmol) was dissolved in DMF (8 ml), pyrrolidine (1.14 g, 16.03 mmol) was added thereto, and the mixture thus obtained was stirred at 40 to 50° C. for 18 hours. Ethyl acetate (100 ml) was added thereto, and the resulting organic layer was washed with a saturated sodium bicarbonate solution (70 ml), water (70 ml) and brine (70 ml) in this order and then dried over anhydrous sodium sulfate. The solvent was removed by evaporation under a reduced pressure, and the crude product thus obtained was purified by silica gel column chromatography (chloroform:methanol=20:1) to obtain the objective compound as a colorless oily material (1.21 g, yield: 85.5%).

TLC Rf: 0.20 (CHCl$_3$:MeOH=20:1), 0.20 (AcOEt); $^1$H-NMR (CDCl$_3$) δ: 7.39–7.24 (10H, m, aromatic), 5.06–5.02 (2H, m, CH$_2$—O—CO), 4.99 (1H, d, J=3.91 Hz, H-1), 4.07 (1H, m, H-2), 2.9–2.6 (6H, m, (CH$_2$)$_3$N), 1.83–1.74 (4H, m, H-3', H-4'); $^{13}$C-NMR(CDCl$_3$) δ: 156.0, 140.8, 136.5, 128.4, 128.2, 128.0, 127.8, 127.4, 126.1, 75.7, 66.6, 58.1, 55.2, 53.4, 23.6

Example 32
Synthesis of (1R, 2R)-2-benzyloxycarbonylamino-3-cyclopentylamino-1-phenyl-1-propanol:

(1R,2R)-2-Benzyloxycarbonylamino-1-phenyl-1,3-propanediol-3-methanesulfonyl ester (1.21 g, 3.19 mmol) was dissolved in DMF (6 ml), cyclopentylamine (1.09 g, 12.8 mmol) was added thereto, and the mixture thus obtained was stirred at 40 to 50° C. for 32 hours. Further, cyclopentylamine (0.51 g, 5.99 mmol) was added thereto, and the obtained mixture was stirred overnight at 40 to 50° C. After confirming almost completion of the reaction with TLC (ethyl acetate), the reaction solution was mixed with ethyl acetate (100 ml) and the resulting organic layer was washed with a saturated sodium bicarbonate solution (70 ml), water (70 ml) and brine (70 ml) in this order and then dried over anhydrous sodium sulfate. The solvent was removed by evaporation under a reduced pressure, and the crude product thus obtained was purified by silica gel column chromatography (chloroform:methanol=20:1) to obtain the objective compound as a colorless oily material (534.4 mg, yield: 45.7%).

TLC Rf: 0.17 (CHCl$_3$:MeOH=20:1), 0.10 (AcOEt); $^1$H-NMR (CDCl$_3$) δ: 7.35–7.23 (10H, m, aromatic), 5.34 (1H, d, CONH), 5.08 (1H, s, H-1), 4.98 (2H, m, CH$_2$—O—CO), 3.94 (1H, m, H-2), 3.24 (1H, m, H-3A), 3.08 (1H, m, H-2'), 2.85 (1H, dd, J=2.93, 12.21 Hz, H-3B), 2.04–1.93, 1.87–1.79, 1.73–1.55, 1.51–1.30 (8H, m, H-3', H-4', H-5', H-6'); $^{13}$C-NMR(CDCl$_3$) δ: 160.7, 141.0, 136.4, 128.4, 128.2, 128.0, 127.8, 127.3, 125.6, 76.3, 66.6, 59.9, 54.7, 53.5, 49.9, 34.1, 33.2, 33.1, 32.7, 23.8, 23.6, 23.4

Example 33
Synthesis of (1R,2R)-2-benzyloxycarbonylamino-3-piperidino-1-phenyl-1-propanol:

(1R,2R)-2-Benzyloxycarbonylamino-1-phenyl-1,3-propanediol-3-methanesulfonyl ester (1.21 g, 3.19 mmol) was dissolved in DMF (6 ml), piperidine (1.09 g, 12.8 mmol) was added thereto, and the mixture thus obtained was stirred at 40 to 50° C. for 24 hours. After confirming almost completion of the reaction with TLC (ethyl acetate, chloroform:methanol=20:1), ethyl acetate (100 ml) was added thereto, and the resulting organic layer was washed with a saturated sodium bicarbonate solution (70 ml), water (70 ml) and brine (70 ml) in this order and then dried over anhydrous sodium sulfate. The solvent was removed by evaporation under a reduced pressure, and the crude product thus obtained was purified by silica gel column chromatography (ethyl acetate) to obtain the objective compound as a colorless oily material (795.4 mg, yield: 68.0%).

TLC Rf: 0.20 (CHCl$_3$:MeOH=20:1), 0.17 (AcOEt); $^1$H-NMR (CDCl$_3$) δ: 7.36–7.25 (10H, m, aromatic), 5.04 (2H, s, CH$_2$—O—CO), 5.01 (1H, d, J=3.42 Hz, H-1), 4.94 (1H, d, J=7.33 Hz, NH), 4.15 (1H, m, H-2), 2.64–2.45 (6H, m, (CH$_2$)$_3$N), 1.68–1.54 (4H, m, H-3', H-5'), 1.5–1.4 (2H, m, H-4'); $^{13}$C-NMR (CDCl$_3$) δ: 155.9, 140.8, 136.4, 128.5, 128.3, 128.1, 127.9, 127.4, 126.3, 75.7, 66.7, 60.5, 55.8, 51.7, 26.1, 23.9

Example 34
Synthesis of (1R, 2R)-2-benzyloxycarbonylamino-3-cyclohexylamino-1-phenyl-1-propanol:

(1R,2R)-2-Benzyloxycarbonylamino-1-phenyl-1,3-propanediol-3-methanesulfonyl ester (1.21 g, 3.19 mmol)

was dissolved in DMF (6 ml), cyclohexylamine (1.29 g, 13.0 mmol) was added thereto, and the mixture thus obtained was stirred at 40 to 50° C. for 2 days. Further, cyclohexylamine (0.62 g, 6.25 mmol) was added thereto, and the obtained mixture was stirred overnight at 40 to 50° C. After confirming almost completion of the reaction with TLC (ethyl acetate, chloroform:methanol=20:1), ethyl acetate (100 ml) was added thereto, and the resulting organic layer was washed with a saturated sodium bicarbonate solution (70 ml), water (70 ml) and brine (70 ml) in this order and then dried over anhydrous sodium sulfate. The solvent was removed by evaporation under a reduced pressure, and the thus obtained crude product was purified by silica gel column chromatography (ethyl acetate) to obtain the objective compound as a colorless oily material (750.0 mg, yield: 61.5%).

TLC Rf: 0.19 ($CHCl_3$:MeOH=20:1), 0.12 (AcOEt); $^1$H-NMR ($CDCl_3$) δ: 7.35–7.22 (10H, m, aromatic), 5.32 (1H, d, J=7.32 Hz, CONH), 5.07 (1H, s, H-1), 4.98 (2H, m, $CH_2$—O—CO), 3.94 (1H, m, H-2), 3.26 (1H, m, H-3A), 2.88 (1H, dd, J=2.44, 12.69 Hz, H-3B), 2.44 (1H, m, H-2'), 1.95–1.86, 1.77–1.68, 1.63–1.60, 1.42–1.02 (10H, m, H-3', H-4', H-5', H-6', H-7'); $^{13}$C-NMR($CDCl_3$) δ: 156.2, 141.0, 136.4, 128.4, 128.2, 128.0, 127.8, 127.3, 125.7, 76.3, 66.6, 56.8, 54.7, 49.6, 47.0, 34.7, 33.5, 33.3, 33.0, 25.9, 25.4, 25.0, 24.8, 24.7

Example 35
Synthesis of (1S,2S)-2-t-butoxycarbonylamino-3-morpholino-1-phenyl-1-propanol:

(1S,2S)-2-t-Butoxycarbonylamino-1-phenyl-1,3-propanediol was mesylated in the same manner as in Example 1 and a morpholine substitution reaction was conducted in the same manner as in Example 3 to obtain the objective compound as a colorless oily material (yield: 63%).

TLC Rf: 0.36 ($CHCl_3$:MeOH=20:1); $^1$H-NMR ($CDCl_3$) δ: 7.38–7.26 (5H, m, aromatic), 4.98 (1H, d, J=3.91 Hz, H-1), 4.05 (1H, m, H-2), 3.74 (4H, m, $(CH_2)_2$O), 2.64–2.59 (5H, m, H-2', H-6', H-3A), 2.46 (1H, dd, J=4.89, 13.19 Hz, H-3B), 1.38 (9H, s, $(CH_3)_3$)

Example 36
Synthesis of (1S,2S)-2-decanoylamino-3-morpholino-1-phenyl-1-propanol using (1S,2S)-2-t-butoxycarbonylamino-3-morpholino-1-phenyl-1-propanol as the raw material:

(1S,2S)-2-t-Butoxycarbonylamino-3-morpholino-1-phenyl-1-propanol (49.9 mg, 0.149 mmol) was dissolved in methylene chloride (1 ml), and trifluoroacetic acid (1 ml) was added thereto under ice cooling. Thirty minutes thereafter, completion of the reaction was confirmed with TLC (chloroform:methanol=9:1), ether (3 ml) was added thereto, and the solvent was removed by evaporation under a reduced pressure. The colorless oily material thus obtained was acylated in the same manner as in Example 7 to obtain the objective compound as a colorless oily material (48.8 mg, yield: 82.2%).

Example 37
Synthesis of (1S,2S)-2-benzyloxycarbonylamino-3-(N-methylpiperazino)-1-phenyl-1-propanol:

(1S,2S)-2-Benzyloxycarbonylamino-1-phenyl-1,3-propanediol-3-methanesulfonyl ester (1.81 g, 4.78 mmol) was dissolved in ethanol (40 ml), sodium iodide (712.8 mg, 4.75 mmol) and N-methylpiperazine (1.92 g, 19.2 mmol) were added thereto, and the mixture thus obtained was stirred at 50° C. for 5 days. After confirming almost completion of the reaction with TLC (chloroform:methanol=9:1), the solvent was removed by evaporation, water (50 ml) and ethyl acetate (100 ml) were added thereto, and the resulting organic layer was washed with water and brine in this order, dried over anhydrous sodium sulfate and then filtered. The solvent was removed by evaporation, and the resulting residue was purified by silica gel column chromatography (chloroform:methanol=20:1) to obtain the objective compound as a colorless oily material (242.2 mg, yield: 13.2%).

TLC Rf: 0.38 ($CHCl_3$:MeOH=9:1); $^1$H-NMR ($CDCl_3$) δ: 7.36–7.26 (10H, m, aromatic), 5.04 (2H, s, $CH_2$—O—CO), 5.00 (1H, d, J=3.41 Hz, H-1), 4.97 (1H, d, NH), 4.12 (1H, m, H-2), 2.70–2.49 (10H, m, $(CH_2)_3$N, $(CH_2)_2$N), 2.28 (3H, s, $CH_3$—N); $^{13}$C-NMR($CDCl_3$) δ: 156.0, 140.7, 136.4, 128.5, 128.3, 128.1, 127.9, 127.5, 126.2, 75.3, 66.8, 59.6, 55.1, 54.1, 52.1, 45.9

Example 38
Synthesis of (1S,2S)-2-benzyloxycarbonylamino-3-((2S)-2-hydroxymethylpyrrolidino)-1-phenyl-1-propanol:

(2S)-2-Hydroxymethylpyrrolidine (323.3 mg, 3.20 mmol) was dissolved in ethanol (12 ml), and the obtained mixture was added dropwise to a methylene chloride solution (3 ml) of (1S,2S)-2-benzyloxycarbonylamino-1-phenyl-1,3-propanediol-3-p-bromobenzenesulfonyl ester (782 mg, 1.50 mmol). Two days after stirring at 45° C., almost completion of the reaction was confirmed with TLC (chloroform:methanol=9:1, ethyl acetate:2-propanol=2:1), the solvent was removed by evaporation, and the resulting residue was purified by silica gel column chromatography (ethyl acetate:2-propanol=7:3) to obtain the objective compound as a colorless oily material (79.5 mg, yield: 13.8%).

TLC Rf: 0.25 ($CHCl_3$:MeOH=9:1), 0.39 (AcOEt: $(CH_3)_2$CHOH=2:1); $^1$H-NMR ($CDCl_3$) δ: 7.51–7.23 (10H, m, aromatic), 5.32 (1H, br, NH), 4.99 (3H, m, H-1, $CH_2$—O—CO), 3.93 (1H, m, H-2), 3.67, 3.66, 3.64, 3.63 (1H, dd, $CH_2$(A)—OH), 3.51 (1H, dd, J=4.40, 11.23 Hz, $CH_2$(B)—OH), 3.28–3.23 (1H, m, H-5'A), 3.08 (1H, dd, J=5.86, 13.19 Hz, H-3A), 2.81 (1H, dd, J=2.93, 13.18 Hz, H-3B), 2.71 (1H, m, H-2'), 2.34–2.28 (1H, m, H-5'B), 1.90–1.59 (4H, m, H-3', H-4'); $^{13}$C-NMR($CDCl_3$) δ: 156.5, 141.0, 136.5, 128.4, 128.3, 128.0, 127.8, 127.5, 125.8, 75.4, 66.6, 66.4, 63.7, 58.0, 56.2, 55.4, 27.0, 23.8

Example 39
Synthesis of (1S,2S)-2-benzyloxycarbonylamino-3-(3-hydroxypyrrolidino)-1-phenyl-1-propanol:

(1S,2S)-2-Benzyloxycarbonylamino-1-phenyl-1,3-propanediol-3-methanesulfonyl ester (2.60 g, 6.86 mmol) was dissolved in ethanol (20 ml), 3-hydroxypyrrolidine (1.19 g, 13.68 mmol) was added thereto, and the mixture thus obtained was stirred at 45° C. for 5 days. After confirming almost completion of the reaction with TLC (chloroform:methanol=9:1), the solvent was removed by evaporation, and the resulting residue was purified by silica gel column chromatography (chloroform:methanol=9:1, ethyl acetate:methanol=9:1) to obtain the objective compound as a colorless oily material (527.1 mg, yield: 20.8%).

TLC Rf: 0.25 ($CHCl_3$:MeOH=9:1), 0.35 (AcOEt:MeOH= 4:1); $^1$H-NMR ($CDCl_3$) δ: 7.41–7.24 (10H, m, aromatic), 5.26 (0.7H, d, J=7.82 Hz, NH, originated from one diastereomer), 5.20 (0.3H, d, NH, originated from the other diastereomer), 5.00 (3H, s, H-1, $CH_2$—O—CO), 4.34 (0.7H, m, H-3', originated from one diastereomer), 4.28 (0.3H, m, H-3', originated from the other diastereomer), 4.02 (1H, m, H-2), 3.04–2.99, 2.89–2.42 (6H, m, $(CH_2)_3$N), 2.20–2.07 (1H, m, H-4'A), 1.80–1.68 (1H, m, H-4'B); $^{13}$C-NMR ($CDCl_3$) δ: 156.5, 141.2, 141.1, 136.7, 128.8, 128.3, 128.2, 127.8, 126.4, 75.4, 75.2, 71.3, 67.0, 64.0, 58.0, 54.2, 54.1, 53.8, 34.9

Example 40

Synthesis of (1S,2S) -2-benzyloxycarbonylamino-3-pyrrolidino-1-phenyl-1-propanol:

(1S,2S)-2-Benzyloxycarbonylamino-1-phenyl-1,3-propanediol-3-methanesulfonyl ester (1.21 g, 3.19 mmol) was dissolved in DMF (6 ml), pyrrolidine (0.91 g, 12.8 mmol) was added thereto, and the obtained mixture was stirred at 40° C. for 24 hours. Ethyl acetate (100 ml) was added thereto, and the resulting organic layer was washed with a saturated sodium bicarbonate solution (70 ml), water (70 ml) and brine (70 ml) in this order and then dried over anhydrous sodium sulfate. The solvent was removed by evaporation under a reduced pressure, and the crude product thus obtained was purified by silica gel column chromatography (chloroform:methanol=20:1) to obtain the objective compound as a colorless oily material (983.1 mg, yield: 87.0%).

TLC Rf: 0.20 (CHCl$_3$:MeOH=20:1), 0.20 (AcOEt); $^1$H-NMR (CDCl$_3$) δ: Coincided with the data of Example 31.

$^{13}$C-NMR(CDCl$_3$) δ: Coincided with the data of Example 31.

Example 41

Synthesis of (1S, 2S) -2-benzyloxycarbonylamino-3-(3-hydroxymethylpiperidino)-1-phenyl-1-propanol:

(1S,2S)-2-Benzyloxycarbonylamino-1-phenyl-1,3-propanediol-3-methanesulfonyl ester (2.43 g, 6.41 mmol) was dissolved in ethanol (20 ml), 3-hydroxymethylpiperidine (1.47 g, 12.78 mmol) was added thereto, and the mixture thus obtained was stirred at 45° C. for 5 days. After confirming almost completion of the reaction with TLC (chloroform:methanol=9:1), the solvent was removed by evaporation, and the resulting residue was purified by silica gel column chromatography (chloroform:methanol=20:1, ethyl acetate:methanol=20:1) to obtain the objective compound as a colorless oily material (293.3 mg, yield: 11.5%).

TLC Rf: 0.42 (CHCl$_3$:MeOH=9:1), 0.16 (AcOEt:MeOH=20:1); $^1$H-NMR (CDCl$_3$) δ: 7.35–7.26 (10H, m, aromatic), 5.03 (2H, s, CH$_2$—O—CO), 4.994 (0.5H, d, J=7.81 Hz, H-1, originated from one diastereomer), 4.986 (0.5H, d, J=8.30 Hz, H-1, originated from the other diastereomer), 4.15–4.09 (1H, m, H-2), 3.56–3.45 (2H, m, CH$_2$—OH), 3.00–2.91, 2.75, 2.25–2.00 (4H, m, H-2', H-6'), 2.65–2.59 (1H, m, H-3A), 2.49–2.45 (1H, m, H-3B), 1.82 (1H, m, H-3'), 1.75–1.65, 1.63–1.53, 1.09–1.04 (4H, m, H-4', H-5'); $^{13}$C-NMR(CDCl$_3$) δ: 156.2, 156.1, 140.7, 136.4, 128.5, 128.3, 128.1, 127.9, 127.5, 126.2, 75.4, 75.3, 66.7, 65.7, 65.6, 60.4, 60.3, 60.2, 58.2, 57.5, 55.7, 55.1, 52.0, 38.8, 38.7, 26.6, 24.7, 14.2

Example 42

Synthesis of (1S,2S)-2-benzyloxycarbonylamino-3-(4-hydroxypiperidino )-1-phenyl-1-propanol:

(1S,2S)-2-Benzyloxycarbonylamino-1-phenyl-1,3-propanediol-3-methanesulfonyl ester (273.6 mg, 0.722 mmol) was dissolved in ethanol (3 ml), sodium iodide (119.2 mg, 0.795 mmol) and 4-hydroxypiperidine (171.5 mg, 1.70 mmol) were added thereto, and the mixture thus obtained was stirred at room temperature for 4 days. After confirming almost completion of the reaction with TLC (chloroform:methanol=9:1), 4-hydroxypiperidine (157.0 mg, 1.55 mmol) was added thereto, and the obtained mixture was stirred at 45° C. for 2 days. The solvent was removed by evaporation, and the resulting residue was purified by silica gel column chromatography (chloroform:methanol=20:1) to obtain the objective compound as a colorless oily material (112.6 mg, yield: 40.6%).

TLC Rf: 0.24 (CHCl$_3$:MeOH=9:1); $^1$H-NMR (CDCl$_3$) δ: 7.36–7.25 (10H, m, aromatic), 5.03 (3H, m, CH$_2$—O—CO, NH), 5.00 (1H, d, J=2.93 Hz, H-1), 4.11 (1H, m, H-2), 3.71 (1H, m, H-4'), 2.91, 2.82, 2.64, 2.48, 2.32 (6H, m, (CH$_2$)$_3$N), 1.89 (2H, m, H-3'A, H-5'A), 1.64–1.56 (2H, m, H-3'B, H-5'B); $^{13}$C-NMR(CDCl$_3$) δ: 156.1, 140.7, 136.4, 128.5, 128.3, 128.1, 127.9, 127.5, 126.2, 75.4, 66.9, 66.8, 66.7, 59.5, 52.2, 51.9, 34.4

Example 43

Synthesis of (1S,2R) -2-benzyloxycarbonylamino-3-(4-hydroxypiperidino)-1-phenyl-1-propanol:

(1S,2R)-2-Benzyloxycarbonylamino-1-phenyl-1,3-propanediol-3-methanesulfonyl ester (270.0 mg, 0.712 mmol) was dissolved in ethanol (3 ml), 4-hydroxypiperidine (287.8 mg, 2.85 mmol) was added thereto, and the mixture thus obtained was stirred at 45° C. for 2 days. After confirming almost completion of the reaction with TLC (chloroform:methanol=9:1), the solvent was removed by evaporation, and the resulting residue was purified by silica gel column chromatography (chloroform:methanol=20:1) to obtain the objective compound as a colorless oily material (170.9 mg, yield: 62.5%).

TLC Rf: 0.24 (CHCl$_3$:MeOH=9:1)

Example 44

Synthesis of (1R,2S)-2-benzyloxycarbonylamino-3-(4-hydroxypiperidino)-1-phenyl-1-propanol:

(1R,2S)-2-Benzyloxycarbonylamino-1-phenyl-1,3-propanediol-3-methanesulfonyl ester (273.6 mg, 0.722 mmol) was dissolved in ethanol (3 ml), 4-hydroxypiperidine (291.7 mg, 2.89 mmol) was added thereto, and the mixture thus obtained was stirred at 45° C. for 2 days. After confirming almost completion of the reaction with TLC (chloroform:methanol=9:1), the solvent was removed by evaporation, and the resulting residue was purified by silica gel column chromatography (chloroform:methanol=20:1) to obtain the objective compound as a colorless oily material (184.3 mg, yield: 66.5%).

TLC Rf: 0.24 (CHCl$_3$:MeOH=9:1);

Example 45

Synthesis of (1R,2R)-2-benzyloxycarbonylamino-3-(4-hydroxypiperidino)-1-phenyl-1-propanol:

(1R,2R)-2-Benzyloxycarbonylamino-1-phenyl-1,3-propanediol-3-methanesulfonyl ester (295.6 mg, 0.780 mmol) was dissolved in ethanol (3 ml), 4-hydroxypiperidine (315.1 mg, 3.12 mmol) was added thereto, and the mixture thus obtained was stirred at 45° C. for 2 days. After confirming almost completion of the reaction with TLC (chloroform:methanol=9:1), the solvent was removed by evaporation, and the resulting residue was purified by silica gel column chromatography (chloroform:methanol=20:1) to obtain the objective compound as a colorless oily material (179.7 mg, yield: 60.0%).

TLC Rf: 0.24 (CHCl$_3$:MeOH=9:1); $^1$H-NMR (CDCl$_3$) δ: 7.36–7.25 (10H, m, aromatic), 5.03 (3H, m, CH$_2$—O—CO, NH), 5.00 (1H, d, J=2.93 Hz, H-1), 4.11 (1H, m, H-2), 3.71 (1H, m, H-4'), 2.91, 2.82, 2.64, 2.48, 2.32 (6H, m, (CH$_2$)$_3$N), 1.89 (2H, m, H-3'A, H-5'A), 1.64–1.56 (2H, m, H-3'B, H-5'B); $^{13}$C-NMR(CDCl$_3$) δ: 156.1, 140.7, 136.4, 128.5, 128.3, 128.1, 127.9, 127.5, 126.2, 75.4, 66.9, 66.8, 66.7, 59.5, 52.2,
51.9, 34.4

Example 46

Synthesis of (1S,2S)-2-benzyloxycarbonylamino-3-diethanolamino-1-phenyl-1-propanol:

(1S,2S)-2-Benzyloxycarbonylamino-1-phenyl-1,3-propanediol-3-methanesulfonyl ester (1.50 g, 3.96 mmol) was dissolved in ethanol (30 ml), diethanolamine (1.69 g, 16.1 mmol) was added thereto, and the mixture thus obtained was stirred at 45° C. for 5 days. After confirming almost completion of the reaction with TLC (chloroform:methanol=9:1), the solvent was removed by evaporation, and the resulting residue was purified by silica gel column chromatography (chloroform:methanol=9:1) to obtain the objective compound as a colorless oily material (81.1 mg, yield: 5.3%).

TLC Rf: 0.38 (CHCl$_3$:MeOH=9:1); $^1$H-NMR (CDCl$_3$) δ: 7.31–7.21 (10H, m, aromatic), 5.48 (1H, d, J=8.79 Hz, NH), 5.04 (1H, d, J=2.44, H-1), 4.95 (2H, m, CH$_2$—O—CO), 3.89 (1H, m, H-2), 3.64–3.54 (4H, m, N(CH$_2$—CH$_2$—OH)$_2$), 2.79, 2.71–2.53 (6H, m, (CH$_2$)$_3$N) $^{13}$C-NMR(CDCl$_3$) δ: 156.9, 141.5, 136.4, 128.4, 128.3, 128.0, 127.8, 127.4, 125.9, 72.6, 66.7, 59.9, 57.5, 57.3, 55.5

Example 47

Synthesis of (1S, 2S)-2-benzyloxycarbonylamino-3-(4-hydroxycyclohexylamino)-1-phenyl-1-propanol:

(1S,2S)-2-Benzyloxycarbonylamino-1-phenyl-1,3-propanediol-3-methanesulfonyl ester (1.21 g, 3.19 mmol) was dissolved in DMF (6 ml), trans-4-aminocyclohexanol (1.47 g, 12.76 mmol) was added thereto, and the mixture thus obtained was stirred at 50° C. for 3 days. After confirming almost completion of the reaction with TLC (chloroform:methanol=9:1), ethyl acetate (100 ml) was added thereto, and the resulting organic layer was washed with a saturated sodium bicarbonate solution (70 ml), water (70 ml) and brine (70 ml) in this order and then dried over anhydrous sodium sulfate. The solvent was removed by evaporation under a reduced pressure, the crude product thus obtained was purified by silica gel column chromatography (chloroform:methanol=9:1) to obtain the objective compound as white crystals (571.5 mg, yield: 45.0%).

TLC Rf: 0.18 (CHCl$_3$:MeOH=4:1), 0.16 (AcOEt:MeOH=4:1); $^1$H-NMR (CDCl$_3$) δ: 7.34–7.23 (10H, m, aromatic), 5.33 (1H, d, NH), 5.07 (1H, s, H-1), 4.98 (2H, m, CH$_2$—O—CO), 3.96 (1H, m, H-2), 3.60 (1H, m, H-4'), 3.25 (1H, m, H-3A), 2.89 (1H, m, H-3B), 2.48 (1H, m, H-1'), 1.97 (4H, m, H-2'A, H-3A, H-5'A, H-6'A), 1.33–1.14 (4H, m, H-2'B, H-3'B, H-5'B, H-6'B); $^{13}$C-NMR(CDCl$_3$) δ: 156.2, 140.8, 136.3, 128.5, 128.3, 128.1, 127.8, 127.4, 125.6, 75.8, 70.0, 66.7, 56.2, 54.7, 49.7, 33.7, 30.9, 30.7

Example 48

Synthesis of (1S,2S)-2-octyloxycarbonylamino-3-morpholino-1-phenyl-1-propanol:

(1S,2S)-2-Amino-3-morpholino-1-phenyl-1-propanol (627.7 mg, 2.66 mmol) was dissolved in methanol (10 ml), triethylamine (0.518 ml, 3.723 mmol) was added thereto at room temperature, chloroformic acid n-octyl ester (0.625 ml, 3.192 mmol) was further added thereto on an ice bath, and the mixture thus obtained was stirred at room temperature for 15 hours. After completion of the reaction, methanol (5 ml) was added thereto, the obtained mixture was stirred for 20 minutes, and then the solvent was removed by evaporation under a reduced pressure. Ethyl acetate (100 ml) was added thereto, and the organic layer thus obtained was washed with each 70 ml of a saturated sodium bicarbonate solution, water and brine in this order. The resulting organic layer was dried over anhydrous sodium sulfate, and then filtered, and the solvent was removed by evaporation under a reduced pressure. The crude product thus obtained was purified by silica gel column chromatography (n-hexane:ethyl acetate=1:2) to obtain the objective compound as a colorless oily material (814.5 mg, yield: 78.1%).

TLC Rf: 0.21 (n-Hexane:AcOEt=1:2), 0.32 (CHCl$_3$:MeOH=20:1), 0.36 (AcOEt); $^1$H-NMR (CDCl$_3$) δ: 7.38–7.26 (5H, m, aromatic), 4.99 (1H, d, J=3.42 Hz, H-1), 4.08 (1H, m, H-2), 3.98 (2H, m, COOCH$_2$), 3.73 (4H, m, (CH$_2$)$_2$O), 2.66–2.45 (6H, m, CH$_2$N(CH$_2$)$_2$), 1.54 (2H, m, COOCH$_2$CH$_2$), 1.27 (10H, m, (CH$_2$)$_5$CH$_3$), 0.88 (3H, t, CH$_2$CH$_3$); $^{13}$C-NMR(CDCl$_3$) δ: 156.5, 140.7, 128.3, 127.6, 126.2, 75.4, 66.9, 65.3, 60.1, 54.4, 52.0, 31.7, 29.2, 29.0, 28.9, 25.7, 22.6, 14.0

Example 49

Synthesis of (1R,2R)-2-octyloxycarbonylamino-3-pyrrolidino-1-phenyl-1-propanol:

(1R,2R)-2-Amino-3-pyrrolidino-1-phenyl-1-propanol (250.2 mg, 1.11 mmol) was dissolved in methanol (5 ml), triethylamine (0.186 ml, 1.337 mmol) was added thereto at room temperature, and chloroformic acid n-octyl ester (0.240 ml, 1.226 mmol) was added thereto on an ice bath, and the mixture thus obtained was stirred at room temperature. Ninety minutes thereafter, triethylamine (0.186 ml, 1.337 mmol) and chloroformic acid n-octyl ester (0.240 ml, 1.226 mmol) were added thereto, and the obtained mixture was stirred at room temperature. Twenty hours thereafter, the solvent was removed by evaporation under a reduced pressure, ethyl acetate (100 ml) was added thereto, and the organic layer thus obtained was washed with each 70 ml of a saturated sodium bicarbonate solution, water and brine in this order, dried over anhydrous sodium sulfate, and then filtered. The solvent was removed by evaporation under a reduced pressure, and the crude product thus obtained was purified by silica gel column chromatography (chloroform:methanol=20:1) to obtain the objective compound as a colorless oily material (99.5 mg, yield: 23.8%).

TLC Rf: 0.28 (AcOEt:MeOH4:1), 0.30 (CHCl$_3$:MeOH=9:1); $^1$H-NMR (CDCl$_3$) δ: 7.36–7.24 (5H, m, aromatic), 5.05 (1H, d, J=2.93 Hz, H-1), 4.9 (1H, d, NH), 4.04 (1H, m, H-2), 3.96 (2H, m, COOCH$_2$), 2.91–2.68 (6H, m, CH$_2$N(CH$_2$)$_2$), 1.80 (4H, m, H-3', H-4'), 1.52 (2H, m, COOCH$_2$CH$_2$), 1.26 (10H, m, (CH$_2$)$_5$CH$_3$), 0.88 (3H, t, CH$_2$CH$_3$); $^{13}$C-NMR(CDCl$_3$) δ: 156.4, 140.9, 128.2, 127.3, 126.1, 75.6, 65.1, 58.1, 55.2, 53.3, 31.7, 29.1, 28.9, 25.7, 23.6, 22.6, 14.0

Example 50

Synthesis of (1R,2R)-2-decylamino-3-pyrrolidino-1-phenyl-1-propanol:

(1R,2R)-2-Decanoylamino-3-pyrrolidino-1-phenyl-1-propanol (181.8 mg, 0.486 mmol) was dissolved in methylene chloride (5 ml), lithium aluminum hydride (153.0 mg, 4.032 mmol) was added thereto at room temperature, and the mixture thus obtained was subjected to reflux at 35 to 40° C. for 2.5 hours. Hydrochloride (1N, 15 ml) was added thereto on an ice bath, and the obtained mixture was stirred for 30 minutes. Further, a saturated sodium bicarbonate solution (70 ml) and chloroform (100 ml) were added thereto, and the organic layer thus obtained was washed with each 70 ml of water and brine in this order, dried over anhydrous sodium sulfate and then filtered. The solvent was removed by evaporation under a reduced pressure, and the crude product thus obtained was purified by silica gel column chromatography (chloroform:methanol=20:1, ethyl acetate:methanol=2:1) to obtain the objective compound as a colorless oily material (121.2 mg, yield: 69.3%).

TLC Rf: 0.39 (CHCl$_3$:MeOH=9:1), 0.19 (AcOEt:MeOH=2:1); $^1$H-NMR (CDCl$_3$) δ: 7.37–7.22 (5H, m, aromatic), 4.68 (1H, d, J=3.90 Hz, H-1), 2.99 (1H, m, H-2), 2.63–2.42 (8H, m, CH$_2$N(CH$_2$)$_2$, NHCH$_2$), 1.77 (4H, m, H-3', H-4'), 1.41–1.24 (16H, m, (CH$_2$)$_8$CH$_3$), 0.88 (3H, t, CH$_3$); $^{13}$C-

NMR(CDCl$_3$) δ: 143.1, 128.1, 127.0, 126.2, 73.9, 61.2, 57.6, 54.5, 48.5, 31.9, 30.2, 29.7, 29.6, 29.4, 29.3, 27.1, 23.6, 22.7, 14.1

Example 51

Synthesis of (1S,2S)-2-benzyloxycarbonylamino-3-morpholino-1-cyclohexyl-1-propanol:

(1S,2S)-2-Benzyloxycarbonylamino-1-cyclohexyl-1,3-propanediol-3-methanesulfonyl ester (369.0 mg, 0.958 mmol) was dissolved in a mixture of methylene chloride and methanol (2:1,5 ml), morpholine (0.25 ml, 2.88 mmol) was added thereto at room temperature, and the mixture thus obtained was stirred at 40° C. Twenty hours thereafter, morpholine (0.083 ml, 0.958 mmol) was further added thereto, and the obtained mixture was stirred at 40° C. for 2 days. After confirming completion of the reaction with TLC (n-hexane:ethyl acetate=1:2), the solvent was removed by evaporation under a reduced pressure, a saturated sodium bicarbonate solution (20 ml) was added thereto, and extraction was conducted with chloroform (30 ml×3 times). The resulting organic layer was dried over anhydrous sodium sulfate and then filtered. The solvent was removed by evaporation under a reduced pressure and the resulting residue was purified by silica gel column chromatography (n-hexane:ethyl acetate=1:2) to obtain the objective compound as a colorless oily material (61.1 mg, yield: 17.0%).

TLC Rf: 0.36 (CHCl$_3$:MeOH=20:1), 0.18 (n-Hexane:AcOEt=1:2); $^1$H-NMR (CDCl$_3$) δ: 7.39–7.26 (5H, m, aromatic), 5.11 (2H, m, CH$_2$O—CO), 4.98 (1H, br, NH), 3.85 (1H, m, H-2), 3.67 (4H, m, (CH$_2$)$_2$O), 3.44 (1H, m, H-1), 2.67–2.48 (6H, m, (CH$_2$)$_3$N), 1.86, 1.75, 1.66, 1.53, 1.38, 1.29–1.11 (11H, m); $^{13}$C-NMR(CDCl$_3$) δ: 155.8, 136.4, 128.5, 128.2, 128.0, 127.9, 79.6, 67.0, 66.8, 66.3, 60.9, 54.2, 47.9, 40.6, 29.5, 27.1, 26.4, 26.0, 25.8

Example 52

Synthesis of (1S,2S)-2-decanoylamino-3-morpholino-1-cyclohexyl-1-propanol:

(1S,2S)-2-Benzyloxycarbonylamino-3-morpholino-1-cyclohexyl-1-propanol (62.9 mg, 0.167 mmol) was dissolved in methanol (2 ml), 10% palladium-carbon (17.5 mg, 9.83 mol %) was added thereto, and the mixture thus obtained was stirred overnight in an atmosphere of hydrogen at room temperature. After confirming completion of the reaction with TLC (chloroform:methanol=9:1, n-hexane:ethyl acetate=1:3), palladium-carbon was removed by filtration, and the filtrate was concentrated to obtain a oily material (45.0 mg). The oily material was dissolved in methanol (1 ml), triethylamine (34.8 μl, 0.250 mmol) was added thereto, and decanoyl chloride (41.0 μl, 0.200 mmol) was added dropwise thereto under ice cooling. Tow hours thereafter, completion of the reaction was confirmed with TLC (ethyl acetate, ethyl acetate:methanol=20:1), and then methanol (5 ml) was added thereto and allowed to stand for 20 minutes. The obtained reaction solution was concentrated under a reduced pressure, and then purified by silica gel column chromatography (ethyl acetate:methanol=40:1) to obtain the objective compound as a colorless oily material (25.3 mg, yield: 38.3%).

TLC Rf: 0.32 (CHCl$_3$:MeOH=20:1), 0.28 (Toluene:Acetone=3:1); $^1$H-NMR (CDCl$_3$) δ: 5.63 (1H, d, J=8.30 Hz, NH), 4.13 (1H, m, H-2), 3.69 (4H, m, (CH$_2$)$_2$O), 3.44 (1H, m, H-1), 2.66–2.49 (6H, m, (CH$_2$)$_3$N), 2.20–2.14 (2H, m, CO—CH$_2$), 1.88–1.56, 1.34–1.11 (25H, m), 0.88 (3H, t, CH$_3$); $^{13}$C-NMR(CDCl$_3$) δ: 172.7, 77.6, 66.9, 60.6, 54.3, 46.5, 40.9, 36.9, 31.8, 29.5, 29.4, 29.3, 26.4, 26.1, 25.8, 22.6, 14.1

Example 53

Synthesis of (2S,3S)-2-benzyloxycarbonylamino-1-morpholino-3-octadecanol:

(2S,3S)-2-Benzyloxycarbonylamino-1,3-octadecanediol-1-methanesulfonyl ester (514.4 mg, 1.003 mmol) was dissolved in a mixture of methylene chloride and methanol (2:1,5 ml), morpholine (348 μl, 4.00 mmol) was added thereto at room temperature, and the mixture thus obtained was stirred at 40° C. Three days thereafter, morpholine (100 μl, 1.15 mmol) was further added thereto, and the obtained mixture was stirred at 40° C. for 3 days. The solvent was removed by evaporation under a reduced pressure, a saturated sodium bicarbonate solution (20 ml) was added thereto, and extraction was conducted with chloroform (30 ml). The resulting organic layer was dried over anhydrous sodium sulfate and then filtered. The solvent was removed by evaporation under a reduced pressure and the resulting residue was purified by silica gel column chromatography (n-hexane:ethyl acetate=1:3) to obtain the objective compound as a colorless oily material (50.7 mg, yield: 10.1%).

TLC Rf: 0.35 (n-Hexane:AcOEt=1:3); $^1$H-NMR (CDCl$_3$) δ: 7.39–7.26 (5H, m, aromatic), 5.11 (2H, m, CH$_2$O—CO), 4.99 (1H, br, NH), 4.46–4.11 (1H, m, H-4A), 3.68 (6H, m, (CH$_2$)$_2$O, H-4B, OH), 3.38 (1H, m, H-3), 2.66–2.54 (6H, m, (CH$_2$)$_3$N), 1.50, 1.25 (26H, m, (C$\underline{H}_2$)$_{13}$CH$_3$), 0.88 (3H, t, CH$_3$)

Example 54

Synthesis of (2S,3S)-2-decanoylamino-1-morpholino-3-octadecanol:

(2S,3S)-2-Benzyloxycarbonylamino-1-morpholino-3-octadecanol (59.2 mg, 0.117 mmol) was dissolved in a mixture of methylene chloride and methanol (1:1, 2 ml), 10% palladium-carbon (21.3 mg, 17.0 mol %) was added thereto, and the mixture thus obtained was stirred in an atmosphere of hydrogen. Three hours thereafter, palladium-carbon was removed by filtration, and the filtrate was concentrated to obtain white crystals (39.7 mg). The white crystals (39.7 mg, 0.107 mmol) were dissolved in a mixture of methylene chloride and methanol (1:1, 2 ml), triethylamine (39.0 μl, 0.280 mmol) was added thereto, decanoyl chloride (48.0 μl, 0.234 mmol) was added dropwise thereto under ice cooling, and the mixture thus obtained was stirred at room temperature for 20 hours. The solvent was removed by evaporation under a reduced pressure, and the obtained residue was purified by silica gel column chromatography (ethyl acetate:methanol=40:1) to obtain the objective compound as a colorless oily material (13.9 mg, yield: 22.6%).

TLC Rf: 0.44 (CHCl$_3$:MeOH=20:1), 0.36 (AcOEt:MeOH=40:1); $^1$H-NMR (CDCl$_3$) δ: 5.80 (1H, d, J=6.84 Hz, NH), 3.95 (1H, m, H-2), 3.69 (4H, m, (CH$_2$)$_2$O), 3.58 (1H, m, H-3), 2.55 (6H, m, (CH$_2$)$_3$N), 2.19 (2H, m, CO—CH$_2$), 1.62, 1.41, 1.25 (42H, m), 0.88 (6H, m, CH$_3$); $^{13}$C-NMR(CDCl$_3$) δ: 173.5, 74.9, 66.8, 60.1, 54.0, 50.4, 36.8, 34.0, 31.9, 31.8, 29.7, 29.6, 29.4, 29.3, 29.2, 25.8, 22.7, 14.1

Example 55

Synthesis of (2S,3S)-2-benzyloxycarbonylamino-1-morpholino-3-tridecanol:

(2S,3S)-2-Benzyloxycarbonylamino-1,3-tridecanediol-1-methanesulfonyl ester (556.2 mg, 1.256 mmol) was dissolved in a mixture of tetrahydrofuran and ethanol (1:1, 4 ml), morpholine (330 μl, 3.79 mmol) was added thereto at room temperature, and the mixture thus obtained was stirred at 40° C. Three days thereafter, morpholine (165 μl, 1.90 mmol) was further added thereto, and the obtained mixture was stirred at 40° C. for 3 days. The solvent was removed by evaporation under a reduced pressure, a saturated sodium bicarbonate solution (20 ml) was added thereto, and extraction was conducted with chloroform (30 ml×3 times). The resulting organic layer was dried over anhydrous sodium sulfate and then filtered. The solvent was removed by evaporation under a reduced pressure and the resulting residue was purified by silica gel column chromatography (n-hexane:ethyl acetate=1:2) to obtain the objective compound as a colorless oily material (27.1 mg, yield: 5.0%).

TLC Rf: 0.29 (CHCl$_3$:MeOH=20:1), 0.28 (n-Hexane:AcOEt=1:2); $^1$H-NMR (CDCl$_3$) δ: 7.39–7.25 (5H, m, aromatic), 5.11 (2H, m, CH$_2$O—CO), 4.95 (1H, br, NH), 4.47–4.16 (1H, m, H-4A), 3.85–3.62 (6H, m, (CH$_2$)$_2$O, H-4B, OH), 3.41 (1H, m, H-3), 2.63–2.41 (6H, m, (CH$_2$)$_3$N), 1.52–1.42, 1.26 (16H, m, (C$\underline{H}_2$)$_8$CH$_3$), 0.88 (3H, t, CH$_3$)

Example 56
Synthesis of (2S,3S)-2-decanoylamino-1-morpholino-3-tridecanol:

(2S,3S)-2-Benzyloxycarbonylamino-1-morpholino-3-tridecanol (25.0 mg, 57.6 μmol) was dissolved in methanol (1 ml), 10% palladium-carbon (16.5 mg, 26.9 mol %) was added thereto, and the mixture thus obtained was stirred in an atmosphere of hydrogen. Two hours thereafter, palladium-carbon was removed by filtration, and the filtrate was concentrated to obtain white crystals (18.4 mg). The white crystals (17.3 mg, 57.6 μmol) were dissolved in methanol (0.5 ml), triethylamine (20.0 μl, 0.143 mmol) was added thereto, and decanoyl chloride (24.0 μl, 0.117 mmol) was added dropwise thereto under ice cooling. One hour thereafter, methanol was added thereto and allowed to stand for 15 hours, the solvent was removed by evaporation under a reduced pressure, and the obtained residue was then purified by silica gel column chromatography (ethyl acetate) to obtain the objective compound as a colorless oily material (10.4 mg, yield: 39.8%).

TLC Rf: 0.41 (CHCl$_3$:MeOH=20:1), 0.29 (AcOEt:MeOH=40:1); $^1$H-NMR (CDCl$_3$) δ: 5.80 (1H, d, J=6.34 Hz, NH), 3.95 (1H, m, H-2), 3.69 (4H, m, (CH$_2$)$_2$O), 3.58 (1H, m, H-3), 2.60–2.55 (6H, m, (CH$_2$)$_3$N), 2.19 (2H, m, CO—CH$_2$), 1.62, 1.41, 1.26 (32H, m), 0.88 (6H, m, CH$_3$); $^{13}$C-NMR(CDCl$_3$) δ: 173.5, 74.9, 66.8, 60.1, 54.0, 50.4, 36.8, 34.0, 31.9, 31.8, 29.7, 29.6, 29.5, 29.3, 25.8, 22.7, 14.1

Example 57
Synthesis of (2S,3S)-2-benzyloxycarbonylamino-1-morpholino-3-nonanol:

(2S,3S)-2-Benzyloxycarbonylamino-1,3-nonanediol-1-methanesulfonyl ester (715.7 mg, 1.850 mmol) was dissolved in a mixture of methyl chloride and methanol (2:1, 10 ml), morpholine (480 μl, 5.51 mmol) was added thereto at room temperature, and the mixture thus obtained was stirred at 40° C. Two days thereafter, morpholine (160 μl, 1.84 mmol) was further added thereto, and the obtained mixture was stirred at 40° C. for 2 days. The solvent was removed by evaporation under a reduced pressure, a saturated sodium bicarbonate solution (20 ml) was added thereto, and extraction was conducted with chloroform (30 ml×3 times). The resulting organic layer was dried over anhydrous sodium sulfate and then filtered. The solvent was removed by evaporation under a reduced pressure and the resulting residue was purified by silica gel column chromatography (n-hexane:ethyl acetate=1:2) to obtain the objective compound as a colorless oily material (76.1 mg, yield: 10.9%).

TLC Rf: 0.53 (CHCl$_3$:MeOH=20:1), 0.29 (n-Hexane:AcOEt=1:2)

Example 58
Synthesis of (2S,3S)-2-decanoylamino-1-morpholino-3-nonanol:

(2S,3S)-2-Benzyloxycarbonylamino-1-morpholino-3-nonanol (68.1 mg, 0.180 mmol) was dissolved in methanol (2 ml), 10% palladium-carbon (36.8 mg, 19.2 mol %) was added thereto, and the mixture thus obtained was stirred in an atmosphere of hydrogen. Fifteen hours thereafter, palladium-carbon was removed by filtration, and the filtrate was concentrated to obtain a colorless oily material (55.9 mg). The colorless oily material (43.9 mg, 0.180 mmol) was dissolved in methanol (1 ml), triethylamine (37.6 μl, 0.270 mmol) was added thereto, decanoyl chloride (48.0 μl, 0.234 mmol) was added dropwise thereto under ice cooling, and the mixture thus obtained was stirred at room tempearture for 18 hours. The solvent was removed by evaporation under a reduced pressure, and the obtained residue was purified by silica gel column chromatography (ethyl acetate:methanol= 20:1) to obtain the objective compound as a colorless oily material (6.0 mg, yield: 8.4%).

TLC Rf: 0.42 (CHCl$_3$:MeOH=20:1), 0.44 (AcOEt:MeOH=20:1); $^1$H-NMR (CDCl$_3$) δ: 5.80 (1H, d, J=6.35 Hz, NH), 3.95 (1H, m, H-2), 3.69 (4H, m, (CH$_2$)$_2$O), 3.59 (1H, m, H-3), 2.55 (6H, m, (CH$_2$)$_3$N), 2.19 (2H, m, CO—CH$_2$), 1.62, 1.41, 1.29, 1.28, 1.26 (24H, m), 0.88 (6H, m, CH$_3$); $^{13}$C-NMR(CDCl$_3$) δ: 173.5, 74.9, 66.9, 60.1, 54.0, 50.4, 36.8, 34.0, 31.8, 29.5, 29.4, 29.3, 25.8, 25.7, 22.6, 14.1

While the invention has been described in detail and with reference to specific embodiments thereof, it will be apparent to one skilled in the art that various changes and modifications can be made therein without departing from the spirit and scope thereof.

This application is based on application No. Hei 7-345080 filed in Japan, the content of which is incorporated hereinto by reference.

What is claimed is:

1. An amino alcohol derivative represented by the following formula (2):

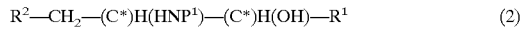

R$^2$—CH$_2$—(C*)H(HNP$^1$)—(C*)H(OH)—R$^1$     (2)

wherein
C* is an asymmetric carbon atom;
P$^1$ is an amino-protecting group selected from the group consisting of benzvloxycarbonyl groups which may have at least one substituent, alkoxycarbonyl groups which may have at least one substituent, and a benzenesulfonyl group;
R$^1$ is an alkyl group, a cycloalkyl group or an aryl group; and
R$^2$ is

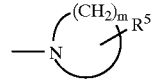

wherein
R$^5$ is a hydrogen atom or at least one substituent, and if two or more said substituents, said substituents are the same or different, wherein said substituent is a hydroxyl group, a lower alkyl group, a lower alkoxyl group, a hydroxyl-lower-alkyl group, a carboxyl group, a (lower alkoxyl) carbonyl group, an aralkyl group, a piperidino group, an acyloxy group, an amino group or an amino-lower-alkyl group; and
m is an integer of 2 to 6.

2. The amino alcohol derivative according to claim 1, wherein
R$^1$ is an alkyl group or a cycloalkyl group, or a phenyl group which may be substituted with from 1 to 3 substituents which are the same or different and are selected from a lower alkyl group, a lower alkoxyl group, a hydroxyl group, a hydroxyl-lower-alkyl group and a nitro group; and $P^1$ is an amino-protecting group selected from (i) a benzyloxycarbonyl group which may be substituted with a nitro group, a halogen atom, a lower alkoxyl group, a (lower alkoxyl)phenylazo group or a phenylazo group and (ii) an alkoxycarbonyl group having a straight, branched or cyclic alkyl group which may be substituted with a fluorenyl group or a methylsulfonyl group.

3. The amino alcohol derivative according to claim 1, wherein $R^1$ is an alkyl group having from 6 to 15 carbon atoms, a cyclohexyl group or a phenyl group;

$P^1$ is an amino-protecting group selected from a benzyloxycarbonyl group, a t-butoxycarbonyl group and an octyloxycarbonyl group; and $R^2$ is an amino group selected from a pyrrolidino group which may be substituted with a hydroxyl group or a hydroxyl-lower-alkyl group or a piperidino group which may be substituted with a hydroxyl group or a hydroxyl-lower-alkyl group.

4. The amino alcohol derivative according to claim 1, wherein $R^1$ is a phenyl group;

$P^1$ is a benzyloxycarbonyl group; and $R^2$ is a pyrrolidino group, a hydroxypyrrolidino group or a hydroxypiperidino group; and the configuration of said derivative is (1S,2S).

5. The amino alcohol derivative according to claim 1, wherein $R^1$ is a phenyl group;

$P^1$ is a benzyloxycarbonyl group; and $R^2$ is a pyrrolidino group or a piperidino group; and the configuration of said derivative is (1R,2R).

6. A process for preparing the amino alcohol derivative defined in any one of claims 1 to 5 which comprises the steps:

(A) reacting an aminopropanol derivative represented by formula (1):

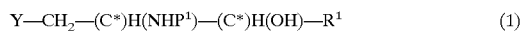

$$Y-CH_2-(C^*)H(NHP^1)-(C^*)H(OH)-R^1 \qquad (1)$$

wherein $C^*$ is an asymmetric carbon atom;

$P^1$ is an amino-protecting group selected from the group consisting of benzyloxycarbonyl groups which may have at least one substituent, alkoxycarbonyl groups which may have at least one substituent, and a benzenesulfonyl group;

$R^1$ is an alkyl group, a cycloalkyl group or an aryl group; and

Y is a leaving group, with an amine represented by $R^2H$, wherein $R^2$ is

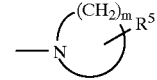

wherein $R^5$ is a hydrogen atom or at least one substituent, and if two or more said substituents, said substituents are the same or different, wherein said substituent is a hydroxyl group, a lower alkyl group, a lower alkoxyl group, a hydroxyl-lower-alkyl group, a carboxyl group, a (lower alkoxyl) carbonyl group, an aralkyl group, a piperidino group, an acyloxy group, an amino group or an amino-lower-alkyl group; and m is an integer of 2 to 6; to obtain an amino alcohol derivative represented by formula (2):

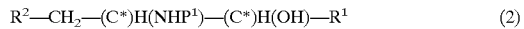

$$R^2-CH_2-(C^*)H(NHP^1)-(C^*)H(OH)-R^1 \qquad (2)$$

wherein $P^1$, $R^1$ and $R^2$ each has the same meaning as defined above.

* * * * *